United States Patent
Gamliel et al.

(10) Patent No.: US 10,495,901 B2
(45) Date of Patent: Dec. 3, 2019

(54) AUTOMATIC EYEWEAR MEASUREMENT AND SPECIFICATION

(71) Applicant: SHAMIR OPTICAL INDUSTRY LTD., Upper Galilee (IL)

(72) Inventors: Avihu Meir Gamliel, Pardes-Hana (IL); Amos Netzer, Ramat-Yohanan (IL); Meirav Metzger Moshe, Ramat-Yohanan (IL); Shai Michael, Ramat-Yohanan (IL)

(73) Assignee: SHAMIR OPTICAL INDUSTRY LTD., Upper Galilee (IL)

( * ) Notice: Subject to any disclaimer, the term of this patent is extended or adjusted under 35 U.S.C. 154(b) by 0 days.

(21) Appl. No.: 15/759,289

(22) PCT Filed: Sep. 12, 2016

(86) PCT No.: PCT/IL2016/051018
§ 371 (c)(1),
(2) Date: Mar. 12, 2018

(87) PCT Pub. No.: WO2017/042824
PCT Pub. Date: Mar. 16, 2017

(65) Prior Publication Data
US 2018/0252942 A1 Sep. 6, 2018

(30) Foreign Application Priority Data

Sep. 12, 2015 (WO) .................. PCT/IB2015/057004

(51) Int. Cl.
*G02C 5/00* (2006.01)
*G02C 13/00* (2006.01)
(Continued)

(52) U.S. Cl.
CPC ............ *G02C 7/027* (2013.01); *A61B 3/0025* (2013.01); *G01P 13/00* (2013.01); *G02C 13/00* (2013.01); *G06F 17/50* (2013.01); *G02C 13/003* (2013.01)

(58) Field of Classification Search
CPC ........ G02C 13/00; G02C 13/003; G02C 5/00; G02C 7/027
(Continued)

(56) References Cited

U.S. PATENT DOCUMENTS

| 7,980,692 B2 | 7/2011 | Fisher et al. |
| 2003/0081173 A1 | 5/2003 | Dreher |

(Continued)

FOREIGN PATENT DOCUMENTS

| WO | 2014015344 | 1/2014 |
| WO | 2015014910 | 2/2015 |

(Continued)

*Primary Examiner* — Darryl J Collins
(74) *Attorney, Agent, or Firm* — Browdy and Neimark, P.L.L.C.

(57) ABSTRACT

A system for automatic eyewear measurement and specification, comprising: at least one mobile sensor carried by a user, a value measurer, in communication with the at least one mobile sensor, configured to measure a plurality of values using the at least one mobile sensor, a behavioral index deriver, in communication with the value measurer, configured to derive at least one behavioral index pertaining to the user, using the measured values, and an eyewear specification generator, in communication with the behavioral index deriver, configured to generate an eyewear specification for the user, using the at least one derived behavioral index.

19 Claims, 12 Drawing Sheets

(51) Int. Cl.
  *G02C 7/02* (2006.01)
  *G06F 17/50* (2006.01)
  *G01P 13/00* (2006.01)
  *A61B 3/00* (2006.01)
(58) Field of Classification Search
  USPC .................. 351/41, 159.75, 159.76, 178
  See application file for complete search history.

(56) References Cited

U.S. PATENT DOCUMENTS

| | | |
|---|---|---|
| 2003/0107707 A1 | 6/2003 | Fisher et al. |
| 2007/0229761 A1 | 10/2007 | Gimenez Carol et al. |
| 2009/0262302 A1 | 10/2009 | Chauveau et al. |
| 2011/0001925 A1 | 1/2011 | Drobe et al. |
| 2011/0128496 A1 | 6/2011 | Giraudet |
| 2013/0147725 A1 | 6/2013 | Chu et al. |
| 2014/0045156 A1 | 2/2014 | Alessandri et al. |
| 2014/0055746 A1 | 2/2014 | Nistico et al. |
| 2015/0055086 A1 | 2/2015 | Fonte et al. |
| 2015/0146168 A1 | 5/2015 | Divo et al. |
| 2015/0160474 A1 | 6/2015 | Chang et al. |
| 2016/0274383 A1* | 9/2016 | Petignaud .............. A61B 3/113 |

FOREIGN PATENT DOCUMENTS

| | | |
|---|---|---|
| WO | 2015027196 | 2/2015 |
| WO | 2015/173388 A2 | 11/2015 |

\* cited by examiner

| Nominal viewing parameters → | Nominal Eye Focusing Distance | Lens region usage parameters | |
|---|---|---|---|
| Activity Type | | Nominal Eye Gaze Direction (pitch relative to the horizon) | Nominal range of Eye Gaze orientation (range of yaw) |
| Driving | 100 meters | 0° | 20° |
| Soccer | 50 meters | -30° | 60° |
| Office/Computer work | 0.7 meters | -10° | 30° |
| . | | | |
| . | | | |

Fig. 6A

| Nominal viewing parameters →<br>User Activity Type | Percentage of the daily duration of the activity |
|---|---|
| Driving | 20% |
| Soccer | 10% |
| Office/Computer work | 70% |
| . | |
| . | |

Fig. 6B

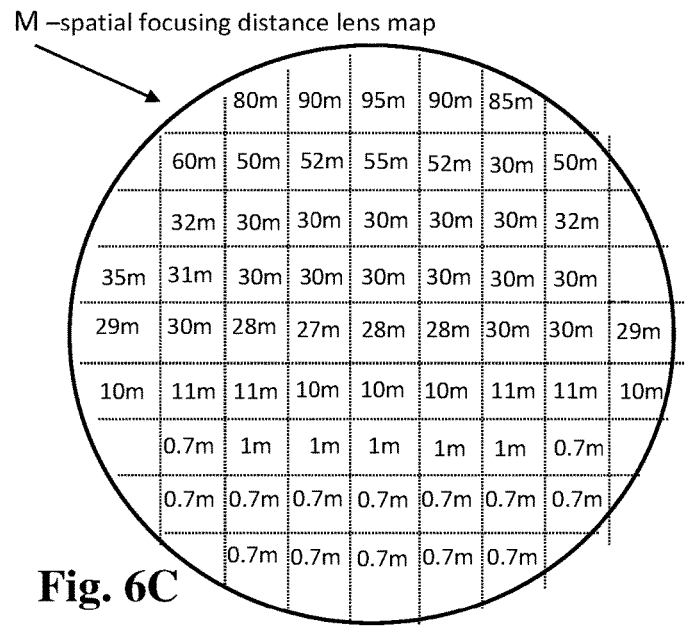

Fig. 6C

AUTOMATIC EYEWEAR MEASUREMENT AND SPECIFICATION

TECHNOLOGICAL FIELD

The present invention relates to eyewear measurement and specification methods and systems.

BACKGROUND

With currently used methods, eyewear specification in general and lenses specification in particular have relied on manual selection which requires active involvement of a customer or an optical store employee, and very often fails to address the customer's real needs.

Optical stores either offer too many options or rather give only few options. Very often, the customer himself does not know what to look for. In particular, customers do not tend to spend much time learning about lens types and lens options. Consequently, customers end up choosing the wrong types of lenses, say types of lenses which are promoted by the store but do not necessarily fit their real needs.

Lens features and compatibility of lenses with prescription determine visual clarity when buying glasses, and is actually the most important part of the whole process of buying glasses. However, in most cases, customers rush through the lens selection process.

Indeed, with an ever increasing number of optional features which the modern optical industry has to offer, the selection of features for eyewear in general, and lenses in particular has become an even more challenging task for both customers and optical industry workers.

U.S. Pat. No. 7,980,692 discloses a technique for selecting and/or designing ophthalmic lenses. This disclosed technique involves the prescribing and/or dispensing ophthalmic lenses, such as progressive addition lenses, for a wearer. Lens usage information is obtained from a wearer and entered into a programmed computer. The programmed computer processes the lens usage information to provide a separate weighted lifestyle score for each of one or more respective lifestyle score categories, such that each weighted lifestyle score is a function of a predetermined relationship between the respective lifestyle score category and at least ophthalmic lens design feature. The programmed computer then selects or designs an ophthalmic lens design using one or more of the weighted lifestyle scores such that the selected or designed ophthalmic lens has at least one lens design feature which has been customized using one or more of the weighted lifestyle scores.

GENERAL DESCRIPTION

There is a need in the art for a novel system and method for designing eyewear for users based on the particular behavioral characteristics of the users. Conventional techniques for designing or selecting eyewear specification from user generally relay on user input information (which is provided orally via interrogation of the user by optical store's personnel or in written form e.g. via questioner filled by the user). However such data provided by the user is typically not sufficient and/or is inaccurate. This results with less than optimal eyewear specification design for the user and/or the plurality of activities with which he may be typically engaged, and/or with incomplete information for determining various aspects/features of the eyewear which are recommended for the user (e.g. the type of recommended frame, the types of lens coatings and/or filters to use and/or desired lens materials, and specific ophthalmic lens design) to match the activities environments and weather lighting conditions with which the user is involved.

To this end the present invention provides a novel technique for generating a recommended eyewear specification of users by monitoring the user's behavior utilizing one or more mobile sensors carried by the user. The technique of the present invention exploits the fact that currently most users carry with them mobile devices such as cellular phones and/or smart garments which include typically a plurality of sensors and/or data connectivity modules. The technique of the present invention elevates this fact by providing a novel systems and methods which can be implemented on the mobile devices of the users and/or on a server system connected thereto and/or in combination thereof. The systems and method according to the invention are adapted to obtain values measured by at least one or a plurality of mobile sensors and processing these values to determine the behavior of the user, its activities and their duration, the weather and lighting conditions he is experiencing and the environments at which he is located during these activities, and utilizing this data to determine one or more recommended eyewear specifications specifically tailored for the user. This all may be achieved reliably without any intervention or data input (which may be biased) from the user.

Thus, according to a broad aspect of the present invention there is provided a system for automatic eyewear measurement and specification. The system includes or is associated with at least one mobile sensor carried by a user; and also includes a value measurer, in communication with the at least one mobile sensor, and configured to measure a plurality of values using the at least one mobile sensor. Additionally the system includes a behavioral index deriver, in communication with the value measurer, configured to derive at least one behavioral index indicative of an eye usage, using the measured values.

The system may be optionally implemented/installable on a mobile device of the user.

According to some embodiments of the present invention the at least one mobile sensor includes sensor(s) typically carried by the user. The sensors may include as at least an accelerometer providing sensory data indicative of the user's activity/motion.

Additionally or alternatively the at least one mobile sensor includes at least a positioning module adapted to provide data indicative of a location of the user. The system may also include a data provider module configured and operable for connecting to data services over a data network to determine at least one of lighting and weather conditions at a location of the user determined by the positioning sensor.

In some embodiments the value measurer is adapted for utilizing the at least one mobile sensor and optionally utilizing the data provider module to determine data indicative of at least one of the following indicators:
- Environment data indicative of an indoors or outdoors environment of the user;
- Lighting conditions at the location of the user;
- Weather conditions at the location of the user;
- Movement of the user.

In some embodiments the system is adapted for activating the at least one mobile sensor at spaced apart time intervals in order to reduce energy consumption of the mobile sensors.

According to some embodiments the behavioral index deriver is adapted for monitoring a behavior of the user during a certain behavioral monitoring time period to determine at least one behavioral index indicative of behavioral characteristics of the user during the certain behavioral monitoring time period. To this end the behavioral index deriver may be adapted for utilizing sensory data obtained from the at least one mobile sensor at spaced apart time intervals during the behavioral monitoring time period; processing the sensory data to determine low level indicators pertaining to behavioral characteristics of the user at the respective time intervals; and processing the low level indicators pertaining to the plurality of time intervals during the monitoring time period to determine the at least one behavioral index indicative of the behavioral characteristics of the user.

According to some embodiments the behavioral index deriver is adapted for determining one or more behavioral indices indicative of one or more of the following behavioral characteristics of the user during a behavioral monitoring period:

Lighting conditions to which the user is exposed;
Types and durations of activities with which the user is engaged.

According to some embodiments of the present invention the system further includes an eyewear specification generator, which is in communication with the behavioral index deriver, and configured to generate an eyewear specification for the user, based on the at least one derived behavioral index. For instance the eyewear specification generator is configured and operable for generating the eyewear specification such that the eyewear specification includes data indicative of at least one recommended eyewear for the user including one or more of the following:

data indicative of at least one optical lens design suitable for the user based on behavioral characteristics of the user;
data indicative of one or more lens coatings selected based on behavioral characteristics of the user;
data indicative of at least one of the following: eyewear frame type and lens material; and wherein the at least one of the eyewear frame type and the lens material is selected based on behavioral characteristics of the user.

To this end the system may be configured and operable for monitoring the user's behavior and generating the eyewear specification for the user by without requiring data input or engagement from the user (namely the user can be passive thorough the process.

According to some embodiments of the present invention the system further includes an eyewear manufacturing specification generator, configured and operable for utilizing the eyewear specification and also personal user data indicative of at least one of an eyesight prescription of the user and face structure of the user and generating an eyewear manufacturing specification for manufacturing at least one piece of eyewear for the user based on the eyewear specification and the personal data.

In some cases the eyewear manufacturing specification generator is adapted for receiving user input data indicative of at least some of the personal data of the user.

According to yet another broad aspect of the present invention there is provided a method for automatic eyewear measurement. The method includes the steps of:

a) measuring values obtained from at least one mobile sensor carried by the user; and
b) processing the measured values and deriving at least one behavioral index indicative of an eye usage using the received data.

According to some embodiments the measuring of the values includes obtaining measured values from at least one mobile sensor including at least one of the following:

an accelerometer providing sensory data indicative of the user's activity;
a positioning module adapted to provide data indicative of a location of the user; and wherein the system includes a data provider module configured and operable for connecting to data services over a data network to determine at least one of lighting and weather conditions at a location of the user determined by the positioning sensor.

According to some embodiments the measuring includes utilizing the data provider module to determine data indicative of at least one of the following indicators:

Environment data indicative of an indoors or outdoors environment of the user;
Lighting conditions at the location of the user;
Weather conditions at the location of the user.

According to some embodiments the method includes activating the at least one mobile sensor at spaced apart time intervals in order to reduce energy consumption of the mobile sensors. To this end the deriving the at least one behavioral index may be based on the values being measured during the spaced apart time intervals.

According to some embodiments the method includes processing the measured values to determine low level indicators pertaining to behavioral characteristics of the user at the respective time intervals. Then processing the low level indicators pertaining to the plurality of time intervals to determine the at least one behavioral index indicative of behavioral characteristics of the user during a behavioral monitoring period extending over a plurality of the time intervals.

In some embodiments the at least one behavioral index includes determining one or more behavioral indices indicative of one or more of the following behavioral characteristics of the user during a behavioral monitoring period:

Lighting conditions to which the user is exposed;
Types and durations of activities with which the user is engaged.

In some embodiments the method further includes generating of an eyewear specification for the user based on the at least one behavioral index derived from the measured values obtained from the at least one mobile sensor.

According to yet another broad aspect of the present invention there is provided a non-transitory computer readable medium storing computer processor executable instructions for performing steps of automatic eyewear measurement, the steps comprising:

a) measuring values obtained from at least one mobile sensor carried by the user; and
b) processing the measured values and deriving at least one behavioral index pertaining to the user use of his eyes, using the received data.

In some implementations the steps further include generating an eyewear manufacturing specification based on the generated eyewear specification.

According to additional implementation the system or method of the invention may be configured and operable as a server system/method configured and operable for connecting (e.g. via wireless communication) to a mobile device/sensor which is typically carried by the user and adapted to monitor the user's behavior via readings/data obtained from the mobile sensor/device, and determine eyewear specification to the user.

To this end, according to yet further broad aspect of the present invention there is provided a system for automatic eyewear measurement and specification, the system include: a data receiver, configured to receive data generated from a plurality of values measured using at least one sensor carried by a user; and an eyewear specification generator, in communication with the data receiver, configured to generate an eyewear specification for the user, using the received data.

According to some embodiments the system further includes a behavioral index deriver, configured to derive at least one behavioral index pertaining to the user, using the received data. The eyewear specification generator is further configured to use the at least one derived behavioral index for generating the eyewear specification. In some cases the system also includes a GUI Manager, configured to present at least one behavioral index pertaining to the user and based on the measured values, to the user, in a GUI (Graphical User Interface).

According to some embodiments the system additionally includes an eyewear manufacturing specification generator, configured and operable for utilizing the eyewear specification and personal user data indicative of at least one of an eyesight prescription of the user and face structure of the user. The eyewear manufacturing specification generator is adapted for generating an eyewear manufacturing specification file in a predefined manufacturing machine readable format, based on the eyewear specification and the personal user data.

In some embodiments the system also includes a value measurer, configured to measure the values using the at least one sensor carried by the user.

According to yet additional broad aspect of the invention there provided a method for automatic eyewear measurement and specification, the method includes the steps of:
a) receiving data generated from a plurality of values measured using at least one sensor carried by a user; and
b) generating an eyewear specification for the user, using the received data. In some cased the method also includes a step of deriving at least one behavioral index pertaining to the user, using the received data. To this end generating of the eyewear specification may be carried out using the at least one derived behavioral index.

In some cased the method also includes a step of generating an eyewear manufacturing specification based on the generated eyewear specification Alternatively or additionally the method includes communicating information based on the generated eyewear specification to a remote party, by which the manufacturing specification may be generated.

In some cases the method also includes values from at least one sensor carried by the user. The sensor may include at least a motion sensor providing sensory data indicative of the user's movement. The method may also include determine an activity of the user based on the measured values. The method may further include utilizing data indicative of a location of the user to determine at least one of lighting and weather conditions at the location of the user by connecting to network data services.

In some implementations at least one of the values obtained from/and/or in relation to the user's mobile device pertain to at least one of the following indicators:
 environment data indicative of an indoors or outdoors environment of the user;
 lighting conditions at the location of the user;
 weather conditions at the location of the user;
 movement of the user.

According to some embodiments the generating eyewear specification includes data indicative of at least one recommended eyewear for the user including one or more of the following:
 data indicative of at least one optical lens design suitable for the user based on behavioral characteristics of the user;
 data indicative of one or more lens coatings selected based on behavioral characteristics of the user;
 data indicative of at least one of the following: eyewear frame type and lens material; and wherein the at least one of the eyewear frame type and the lens material is selected based on behavioral characteristics of the user.

To this end the method/technique of the invention provides for generating of the eyewear specification by monitoring a behavior of the user and without requiring data input from the user.

According to certain embodiments the method further includes generating an eyewear manufacturing specification by carrying out the following: receiving input data including personal user data indicative of at least one of an eyesight prescription of the user and face structure of the user; and utilizing the eyewear specification and personal user data to generating the eyewear manufacturing specification.

According to further yet additional aspect of the present invention there is provided a non-transitory computer readable medium storing computer processor executable instructions for performing steps of automatic eyewear measurement and specification, the steps comprising:
a) receiving data generated from a plurality of values measured using at least one sensor carried by a user; and
b) generating an eyewear specification for the user, using the received data.

In some cases the computer readable medium includes executable instructions for deriving at least one behavioral index pertaining to the user, using the received data, wherein the generating of the eyewear specification for the user is carried out using the at least one derived behavioral index. Alternatively or additionally the computer readable medium includes executable instructions for receiving data indicative of at least one behavioral index pertaining to the user and derived using the measured values.

In some embodiments the computer readable medium also includes executable instructions for generating a file in a predefined manufacturing machine readable format, based on the generated eyewear specification.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof.

Moreover, according to actual instrumentation and equipment of preferred embodiments of the method and system of the present invention, several selected steps could be implemented by hardware or by software on any operating system of any firmware or a combination thereof.

For example, as hardware, selected steps of the invention could be implemented as a chip or a circuit. As software, selected steps of the invention could be implemented as a plurality of software instructions being executed by a computer using any suitable operating system. In any case, selected steps of the method and system of the invention could be described as being performed by a data processor, such as a computing platform for executing a plurality of instructions.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 3A illustrates the operation of the system for deriving behavioral characteristics of the user based on the sensor data, and FIG. 3B illustrates determination of the eyewear specification and optional determination of eyewear production specification based on the behavioral characteristics of the user and optionally also based on user input data indicative of an eyesight prescription and/or facial parameters of the user;

FIGS. 6A to 6E show tables of exemplified reference PAL lens design data and behavioral activities of the user and graphical illustrations of PAL lenses selected and/or designed based on these tables.

Figure 1A:
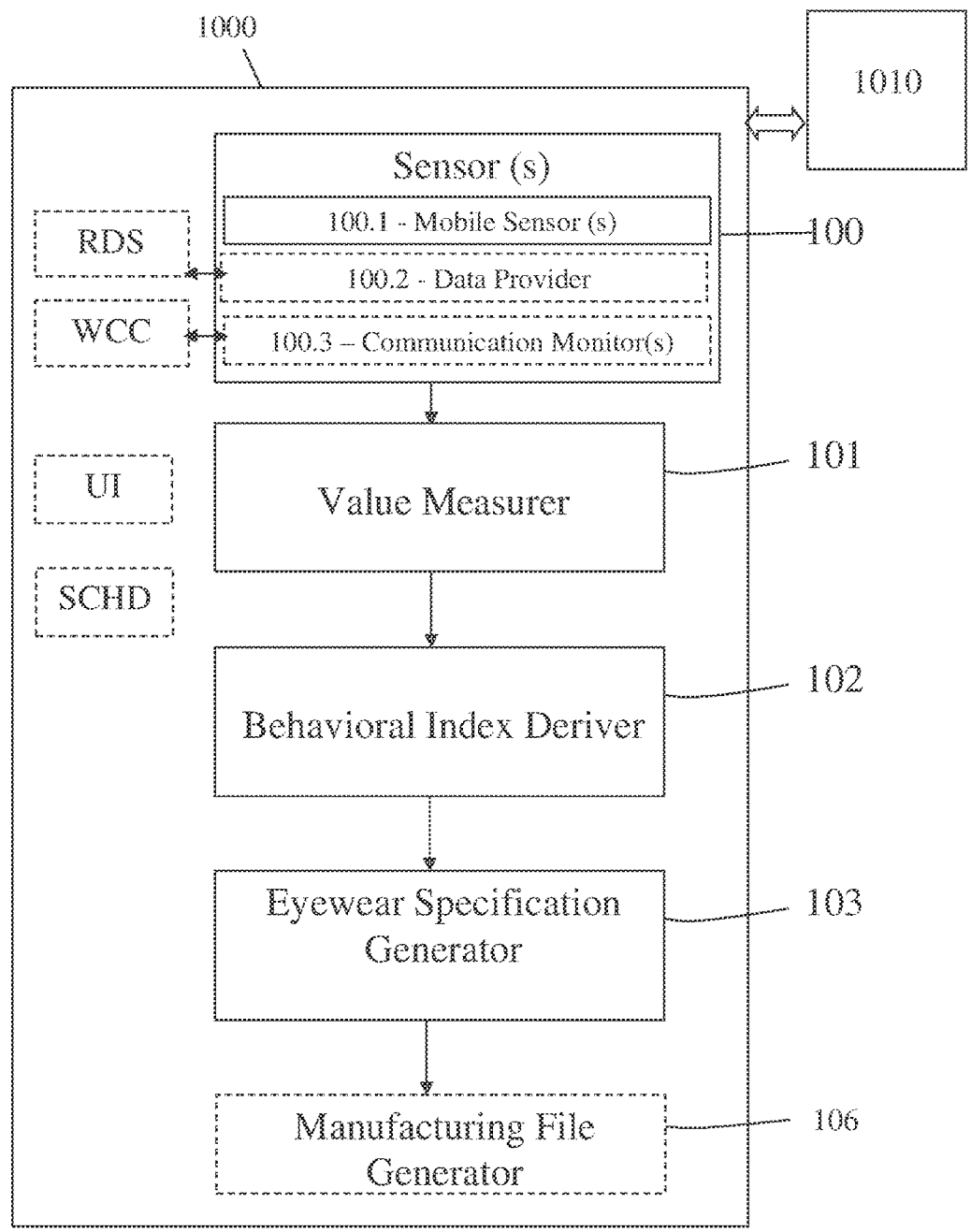
FIGS. 1A and 1B are block diagrams schematically illustrating exemplary systems for automatic eyewear measurement and specification, according to two exemplary embodiments of the present invention.

For clarity similar modules and/or elements and/or method steps and/or features f the invention having like functionalities are designated by like reference numerals in all the figures of the present application. Also optional features and/or modules and/or functions are marked by dashed lines in the figures of the present invention.

DETAILED DESCRIPTION OF EMBODIMENTS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. The description taken with the drawings making apparent to those skilled in the art how the several forms of the invention may be embodied in practice.

The present embodiments comprise a system and a method for automatic eyewear measurement and specification.

Modern eyewear and particularly, optical lenses have a variety of features which may be selected to best fit the different needs of any individual customer, say different types of coatings such as anti-glare coating, anti-fog coating, etc.

Indeed, a careful selection of features for lenses to be used in optical glasses, sun glasses, etc., has the potential to significantly improve the quality of life of any wearer of glasses.

Yet, at optical stores, customers are still either offered too many selections or are rather not given enough choices. Particularly, when it comes to lenses and their features, very often, customers themselves do not know what to look for. Indeed, customers do not tend to spend much time learning about types of lenses and the features which make up the specification of lenses.

Consequently, many customers end up using eyewear with lenses which prove very unsatisfactory, particularly when the lenses lack features which would better fit the needs of a specific customer.

Exemplary embodiments of the present invention introduce a method of passively (i.e. without the user's active involvement in any measurement taken) learning user's way of life, work environment, etc., based on values measured using one or more mobile sensors carried by the user through a time period, say a day of work, a week, or a number (say one or more) of hours.

For example, the method may use one or more of the sensors usually installed on a modern smart phone (say a GPS Receiver, one or more accelerometers, a camera, etc.), and derive one or more behavioral indexes characterizing the smart phone's user, using values measured by those sensors, as described in further detail hereinbelow.

The derived behavioral indexes may pertain to one or more aspects of the user's behavior—say to the user's movement or physical activity (driving, sitting, skiing), to the environment in which the user spends his time (say the user's exposure to blue light emitted from computer screens, to the user's exposure to sun glare, etc.).

Based on the derived behavioral indexes, the method automatically generates an eyewear specification for the user, as described in further detail hereinbelow.

Thus, in a first example, one of the behavioral indexes derived using a temperature sensor or remote (on line) weather services based on the user's location, indicates that during his day of work, the user (say a worker) experiences frequent temperature changes that are likely to result in the user fogging his glasses.

Consequently, in the exemplary method, the eyewear specification generated for the user includes an anti-fog coating on lenses to be used for manufacturing a pair of glasses for the user.

In a second example, based on values measured by one or more accelerometers, one of the behavioral indexes indicates that the user engages in frequent and extensive physical activity (say sport).

Consequently, the eyewear specification generated for the user includes an anti-scratch coating on the lenses or lenses made of a durable material, for preventing user's lenses from scratching or breaking when dropped during the user's extensive physical activity, an elastic strap to be connected to the eyewear (say glasses), etc., as described in further detail hereinbelow.

Thus, potentially, with present embodiments, the eyewear specification may better suit the user's needs as passively learnt from the values measured by the sensors, by taking into consideration passively learnt, hitherto ignored behavioral aspects, in an automatic generation of eyewear specification.

Further, with present embodiments, the eyewear specification may be generated in natural way different from a clinical or an optical testing setting, with the user only having to carry his smart phone, tablet computer, or wearable device (say smart watch) in the usual way most users do on a daily basis.

Further in the exemplary method, the generated eyewear specification may also be communicated to a remote party (say to an optical manufacturer of glasses or lenses).

Thus, in one example, the generated eyewear specification is stored in a file of a format readable by a manufacturing machine (or an array of machines). Say an input file for a manufacturing machine, etc., as described in further detail hereinbelow.

The principles and operation of an apparatus, a method, and a computer readable memory, according to the present invention, may be better understood with reference to the drawings and accompanying description.

Before explaining at least one embodiment of the invention in detail, it is to be understood that the invention is not limited in its application to the details of construction and the arrangement of the components set forth in the following description or illustrated in the drawings.

The invention is capable of other embodiments or of being practiced or carried out in various ways. Also, it is to be understood that the phraseology and terminology employed herein is for the purpose of description and should not be regarded as limiting.

Figure 1B:
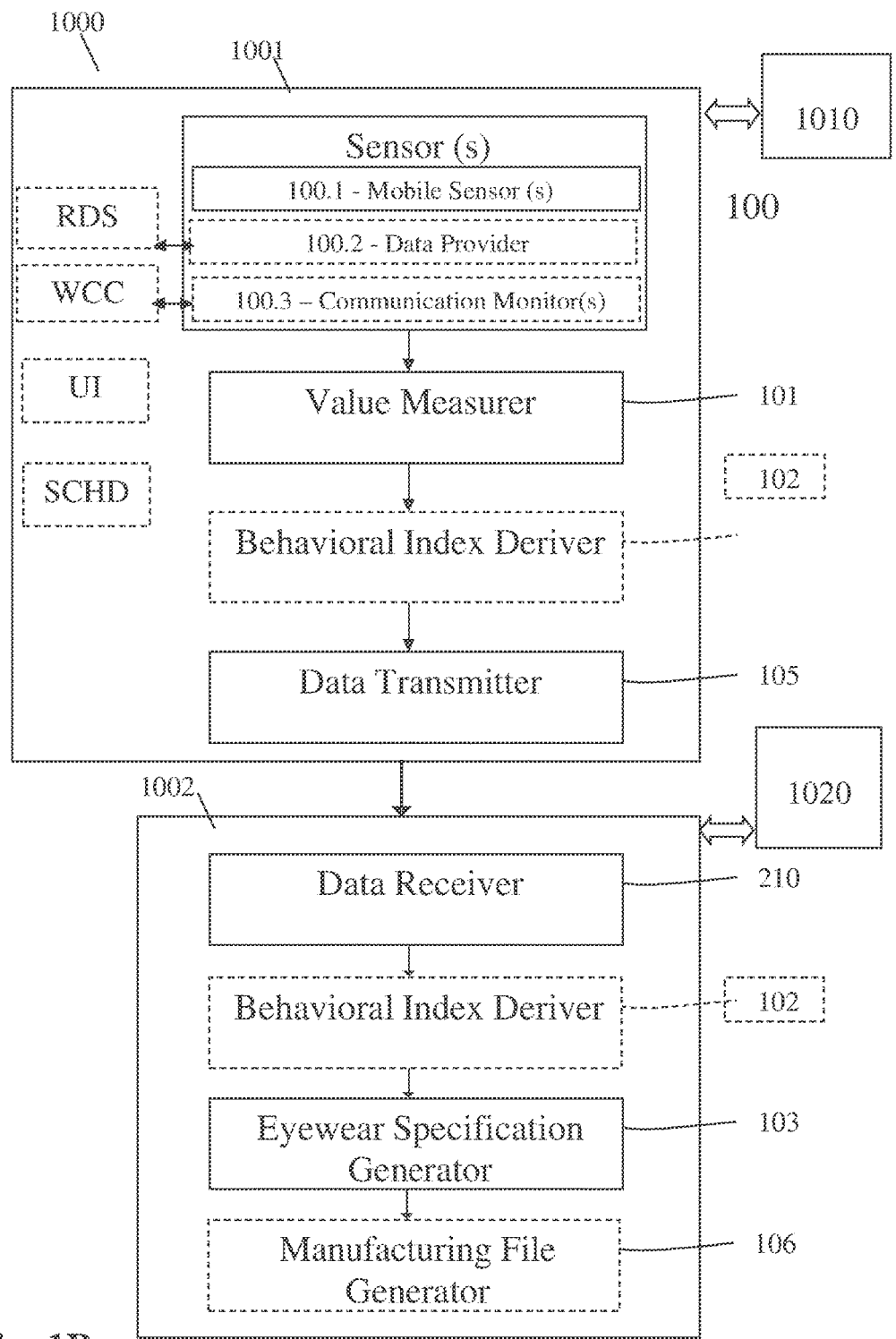

Reference is now made together FIGS. 1A and 1B, which are block diagrams schematically illustrating the configuration of an automatic eyewear measurement and specification systems 1000 (devices/apparatuses), according to exemplary embodiments of the present invention.

An systems for automatic eyewear measurement and specification, according to certain exemplary embodiments of the present invention, may be implemented partially or entirely on a mobile device, such as a smart phone, a tablet computer, a user wearable device (say an Apple® Watch, etc., as known in the art) and/or it may be distributed between one or more mobile devices which may be used the user and a server computer/system.

For instance system 1000, which is illustrated in FIG. 1A, may be implemented entirely on the mobile device 1010. System 1000, which is illustrated in FIG. 1B, is implemented as a distributed system including two sub-systems: sub-system 1001, which is implemented on the mobile device 1010 of the user and is configured and operable at least for acquiring sensor data from sensors included or associated with the mobile device and optionally also processing the sensor data to determine data indicative of the user's behavior (e.g. in the form of behavioral indices as explained in further details below); and sub-system 1002, which is implemented on a remote/server system 1020 connectable via wired or wireless communication to the sub-system 1001 and adapted to receive and process the sensor data or the behavioral indices obtained by sub-system 1001 to determine eyewear specification suitable for the user, and possibly also determine the manufacturing specification thereof.

The system 1000 generally includes or associated with a computer processor and may further include or associated with one or more mobile sensors 100 which are to be carried by the user for a not necessarily consecutive period of one or more hours, days, weeks, etc.

The system 1000 may be partially or entirely implemented in software or hardware components being part or installable on a mobile device. It should be understood that in the context of the present application the phrase mobile device may designate any a modern mobile device such as smart phone or tablet (e.g. an Apple iPhone™), smart garments or other wearable electronic devices which may include or be connectable to one or more sensors and typically also includes data communication modules adapted for communicating data from the mobile device), and optionally also one or more processors and/or computer memories capable of processing and/or storage of data. To this end, the system 1000 may include one or more sensors 100 installed on the mobile device 1010 itself (say sensors as commonly installed on a modern mobile device such as smart phone, tablet, smart garments, wearable electronic devices), one or more mobile sensors 100 worn by the user (e.g. sensors integrated in smart garments) and connected to the mobile device 1010 over a wired or a wireless connection, etc., or any combination thereof, as known in the art.

The mobile device 1010 may further include other hardware and software components, as known in the art of smart mobile devices. For example, the device 1010 may include communications hardware and software components (say drivers and communications cards), for wireless communication to another device or to a wireless network such as a Wireless Local Area Network (WLAN), a Cellular Telephony Network, etc., as known in the art.

Thus, the system 1000 includes the mobile device's computer processor and one or more additional parts/modules as described in further detail hereinbelow, such as the modules denoted 101, 102 and 103 in FIG. 1A and modules 101, 102 and 105 in subsystem 1001 and modules 210, 102 and 103 in subsystem 1002 of FIG. 1B.

The additional parts/modules may be implemented as software, hardware or firmware modules, for example by software application embedded in tangible memory an including computer readable instructions executable by the computer processor to for causing the processor to execute the steps of one of the methods described in further detail hereinbelow.

For example, modules 101-103 may be implemented as a computer application such an application installable on a mobile device 1010 (e.g. smart-phone/tablet application which may be downloaded to the user's mobile device 1010 from an appropriate on-line application store, (e.g. say from the Apple® App Store in case the mobile device 1010 is an iPhone®). Modules 210, 102 and 103 may be implemented as software, hardware or firmware modules installable on the remote server system 1020.

Generally, the system 1000 is configured and operable for monitoring the behavior of the user of the mobile device over a certain monitoring time period (e.g. the monitoring time period may be a predefined time period such as few days/weeks/month(s)) to determine and characterize the user's behavior and generate eyewear specification matching to the identified behavior of the user.

Optionally, the monitoring session which as indicated above continues for a monitoring period of typically, but not necessarily at least several days is initiated triggered by the occurrence of one or more predefined events. For instance a predefined event for starting the user's behavior monitoring session may be initiated by the user, e.g. via a user interface module UI optionally included in the system 1000 or in sub-system 1001 and configured and operable for receiving the user instructions to monitor his behavior. Alternatively or additionally a predefined event for starting the user's behavior monitoring session may be scheduled to operate every predefined periods, for example once in few months (e.g. once every three months). This may be initiated by an optional scheduler module SCHD, which may be included in system 1000.

As will be appreciated by those versed in the art of mobile devices, the operation of the mobile sensors is typically relatively energy consuming. Therefore according to some embodiments of the present invention the system 1000 or at least the sensors 100 are not operated continuously during the monitoring time period at which the monitoring session is carried out. Instead, in order to save battery according to some embodiments of present invention the system 1000, or at least the modules thereof, which are associated with operating one or more of the sensors, are the executed on a periodic basis, for example executed in predetermined time intervals/slots (for instance at intervals of every several minutes, say every five minutes), whereby each time interval may include only few seconds to few tens of seconds of operation the sensors of the mobile device 1010. Since at least some of the sensors are not required to operate continuously but operated in intervals, substantial reduction in the required energy consumption is obtained (as compared to the case the sensors are continuously operated). The resolution of time intervals (e.g. of several minutes) may be sufficient for acquiring sensor data sufficiently accurate for monitoring the user's behavior. To this end the scheduler SCHD may be configured and operable for initiating the periodic operation of the sensors 100 and optionally of other modules of the system 1000.

Thus, in certain embodiments of the present invention the system 1000 includes the one or more sensors 100. Indeed typically at least some of them are sensors 100 are sensors which are installed on the mobile device 1010 itself or one a smart garment connected thereto via data communication such as Bluetooth or WiFi. These may include one or more of the sensors commonly installed on modern smart phones), or is rather connected to the device over a wired or a wireless connection. In some cases the sensors from which data is obtained 100 may also include remote sensors or data sources which provide sensory data. To this end the system 1000 may also include a data provider module 100.2, which is configured and operable for obtaining data from one or more data sources such as weather and light condition data sources available over the network. Typically however, at least some of the sensor, particularly sensors such as accelerometers form which user movements can be determined, are mobile sensors 100.1 which are installed at the mobile device itself or one smart garments of the user. Other sensory data, such as position data, lighting data (e.g. UV levels and sun-glare), weather data (e.g. temperature, humidity) and time data, may be obtained either from locally installed mobile sensors 100.1, which are furnished on the mobile device or its associated smart garments, or obtained by the data provider 100.2 from one or more network information services (remote data services) RDS (e.g. based on the location of the user). In this regards, as for the user's location, this may be typically determined by position systems/sensors (such as GPS receiver) being one of the mobile sensors 100.1 installed on the user's mobile device. However in some cases the location of the user may also be obtained by the data provider 100.2 from location services RDS which may determine the user location for instance based on its mobile devices cellular communication.

In view of the above, essentially the only mobile sensors 100.1 which may be required to be included/associated with the mobile device 1010 of the user are one or more movement sensing sensors, such as an accelerometer sensor and possibly also rotation sensors and/or compass, from which user movement and/or activity type can be determined estimated. Other data relating to the location of the user, and lighting, weather and/or environment to which the user is exposed may be determined according to various embodiments of the present invention by respective mobile sensors 100.1 associated with the mobile device 1010 or obtained by the data provider 100.2 of the system 100 from data services available over the network. Additionally, optionally some environmental data may also be obtained from communication monitor module(s) 100.3 adapted for interrogating the wireless communication modules/cards WCC of the mobile device 1010, to determine the remote gateways (e.g. access-points or cellular antennas) with which the wireless communication modules/cards WCC communicate.

Thus, sensors 100 include at least one or more motion sensing sensors such as accelerometer and/or rotation rate sensors and optionally a positioning sensor/system, and may include a data provider capable of obtaining sensory data from the network (e.g. internet) and/or may further include but are not limited to: a GPS (Global Positioning System) receiver, a photometer, a camera, a compass, a clock, a Wi-Fi communications card, a cellular telephony 3G, 4G, or LTE communications card, etc., as described in further detail hereinbelow.

The exemplary system 1000 further include a value measurer module 101 adapted for receiving data indicative of the readouts of the sensors 100 (e.g. directly via communication with the one or more sensors 100 or indirectly via the operating system of the mobile device 1010 or via the data provider 100.2, which can access remote sensory data pertaining to the location of the mobile device 1010 from the internet/network). The value measurer 101 measures/obtains and stored one or more values using the sensors 100 carried by the user, as described in further detail hereinbelow.

Optionally, one or more of the measured values pertains to the user's movement, as described in further detail hereinbelow, and as illustrated, for example, by FIG. 3A. Typically, the measured values which pertain to the user's movement are obtained from the mobile sensors 100.1 of the mobile device 1010 of the user or from mobile sensors carried by the user and associated/connected to the system 1000 or to the mobile device 1010 via wired or wireless connection (such as data communication). Optionally, one or more of the measured values pertains to the user's environment, as described in further detail hereinbelow and as illustrated, for example, by FIG. 3A. Typically, the measured values which pertain to the user's environment are indicative of whether the user is in-doors or outdoors. These may be inter-alia determined communication monitor module(s) 100.3 by monitoring the wireless data/telephony connection of the user's mobile device (for instance monitoring the state of the WiFi and/or Bluetooth communication and/or monitoring the cellular communication (3G, 4G, or LTE communication). To this end, the mobile device's 1010 communication card(s) also serve as sensors in the sense that the communication data/parameters obtained therefrom (parameters of the cellular and/or Bluetooth and/or WiFi communication therethrough) are indicative of the environment at which the user is located (indoors or outdoors). Optionally, one or more of the measured values pertains to the lighting conditions and possibly also weather conditions, to which the user is exposed, as described in further detail hereinbelow and as illustrated, for example, by FIG. 3A. In this regards it is noted that indeed some lighting conditions and/or weather conditions data may be measured by local sensors residing on the mobile device 100.1 or connectable thereto. However, in some embodiments in order to obtain reliable and accurate results the data indicative of the lighting conditions and/or weather conditions is obtained by utilizing a data provider module 100.2 from remote network services, such as lighting and/or weather conditions services on the internet or other data network (e.g. based on the user's location).

Optionally, the value measurer 101 further records the measured values in one or more logs, as described in further detail hereinbelow.

Optionally, (e.g. during the monitoring period), the value measurer 101 measures at least some of the values, by sampling/querying one or more of the sensors 100 continuously or rather periodically at spaced apart time intervals, say once in a pre-defined period (say once in a minute, one in an hour, etc.), as described in further detail hereinbelow.

Optionally according to some embodiments at each monitoring time interval the value measurer 101 may obtain one or more data samples from the sensors 100. For some sensors 100, (e.g. mobile sensors such as GPS/location sensor and/or from remote data services RDS, such as weather/light/temperature data services associated with the data provider 100.2) obtaining a single sample/data piece pertaining to a at a single point in time may provide data that is sufficiently represents the measured property/condition, which is measured by the respective sensors during the time interval. For instance lighting data obtained from the remote data services RDS for a certain time during the time interval provides sufficient data from which the lightening conditions during that entire time interval can be deduced. To this end the value measurer 101 may be configured and operable to obtain at least one data measurement from such sensors at each time interval.

However, for certain types sensors the property/condition, which should be deduced from the sensors' measurements at each time interval, requires more than one sample of the sensors' measurement at each of the time interval and/or requires a time profile of the sensor's measurement during each time interval. For instance in order to deuce the user's movement type during each time interval, the accelerometer and/or rotation rate sensors should be sampled consecutively during each respective time interval in order to obtain a time pattern/profile of the sensors reading (see for example FIGS. 4A to 4D) from which the user's movement type can be deduced. To this end, in some embodiments, the value measurer 101 is configured and operable to obtain and record, for each monitoring time interval, a time sequence of measured/sampling values from those sensors. As will be further explained in more details below this time sequence/profile is then analyzed (e.g. by the Behavioral Index Deriver 102) to determine low level indicators indicative of the user's behavior and/or his environment conditions during the respective time interval. This is illustrated for example in FIG. 2C.

Optionally, the value measurer 101 measures some of the values, by sampling a specific one of the sensor 100 whenever a pre-defined change occurs in values continuously or periodically measured using a predefined, other one of the sensors 100.), as described in further detail hereinbelow.

Thus, in one example, the value measurer 101 samples the user mobile device's GPS receiver 100 or compass 100 whenever continuously measured accelerometer 100 values exceed a predefined threshold value (say when the user starts running), as described in further detail hereinbelow.

The system 1000 further includes a behavioral index deriver 102, in communication with the value measurer 101. The behavioral index deriver 102 derives one or more behavioral indexes, which pertain to the user, by using the values measured by the value measurer 101, as described in further detail hereinbelow, and as illustrated, for example, in FIG. 3A.

Optionally, the behavioral index deriver 102 further uses one or more databases for deriving the behavioral indexes. The databases may include but are not limited to, for example, databases accessible publically (say over the internet), private databases (say a database already embedded in the computer application), etc., as described in further detail hereinbelow.

For example, according to some embodiments the behavioral index deriver 102 utilizes one or more weather/environmental conditions databases to derive one or more of the following environment/weather parameters existing at the user's location (at the location of the mobile device 1010): the weather (e.g. temperature/cloudiness), UV radiation exposure, temperature. The databases used may include for example weather databases and/or other databases currently available from government agencies and private entities. This is further described in more details hereinbelow.

Optionally, the behavioral index deriver 102 further uses history databases for deriving the behavioral indexes. For example, the behavioral index deriver 102 may use a database of historic values previously measured using one or more of the sensors, a database of historic data obtained from the weather, UV radiation exposure, temperature, or other databases, etc. as described in further detail hereinbelow.

Optionally, the behavioral index deriver 102 further records the derived behavioral indexes in one or more logs, as described in further detail hereinbelow.

According to some embodiments of the present invention the system 1000 further includes an eyewear specification generator 103, in communication with the behavioral index deriver 102.

The eyewear specification generator 103 generates an eyewear specification for the user, using the behavioral indexes derived by the behavioral index deriver 102, as described in further detail hereinbelow, and as illustrated, for example, in FIG. 3B.

The eyewear specification consists of data which includes but is not limited to one or more features which the user's eyewear (say a pair of glasses to be manufactured or assembled for the specific user) is to have, as described in further detail hereinbelow.

For example, the eyewear specification may specify coating types to be applied to lenses, materials (say plastic type, mineral type (say glass) to be used for manufacturing the lenses), etc., as per the user's needs as automatically learnt from the values measured by the sensors 100, say using the derived behavioral indexes.

The eyewear specification generator 103 may thus generate the eyewear specification based on a passive learning of the user's needs from the user's behavior through a time period of the measuring of the values, say through one of the user's day of work or through a number of hours, as described in further detail hereinbelow.

The eyewear specification generator 103 generates the eyewear specification from the behavioral indexes derived from the values measured using the one or more sensor(s) 100 when being carried by the user (say for one or more days), as described in further detail hereinbelow.

Optionally, the eyewear specification generator 103 further uses one or more databases for generating the eyewear specification. The databases may include, for example, databases accessible publically (say over the internet), private databases (say a specific optical vendor's database already embedded in the computer application, which database that may be updated periodically by the application), etc., as described in further detail hereinbelow.

Optionally, the system 1000 further includes a GUI Manager UI, in communication with the eyewear specification generator 103, the behavioral index deriver 102, or both the eyewear specification generator 103 and the behavioral index deriver 102.

The GUI Manager UI may be configured and operable to present the behavioral indexes pertaining to the user and derived by the behavioral index deriver 102, and or present the generated eyewear specification obtained by eyewear specification generator 103, to the user. The behavioral indexes and/or the generated eyewear specification may be presented on a Graphical User Interface (GUI) of the mobile device 1010, say on a screen of the user's smart cellular phone or smart watch, as described in further detail hereinbelow.

Optionally, according to some embodiments of the present invention the system 1000 further includes a manufacturing file generator 106 in communication with the eyewear specification generator 103. The manufacturing file generator is configured and operable to obtain the generated eyewear specification from the eyewear specification generator 103 and also obtain personal user data indicative of the user's eyesight prescription (e.g. which may be entered by the user as user input received through the UI) and optionally data indicative of the user's face structure (which may also be received from the user e.g. by using a camera of the mobile device to capture an image of the user's face or by using the UI to receive respective textual data indicative of the user's facial structure), and utilize the eyewear specification, the eyesight prescription and the optional face structure data to generate a corresponding manufacturing specification file in a predefined manufacturing machine readable format, which is usable for manufacturing eyewear suitable for the user.

For example, the manufacturing file generator 106 may store the eyewear specification in a file of an input file format used by an eyewear (say lenses) manufacturing machine, a three dimensional (3D) printing system adapted for printing lenses (say from plastic), etc., as known in the art.

In this regards it should be noted that according to various embodiments of the present invention, the generation of the eyewear specification is performed by modules 101 to 103 without requiring any intervention or input from the user. To this end, the user may be completely passive while the system 1000 utilizes the sensors 100 of the mobile device 1010 and monitors, records, and analyzes his behavior during a monitoring period, and then generates (by module 103) an eyewear specification tailored for the user's behavior. Conveniently, the eyewear specification generated in this way does not require any input from the user and can be used together with an eyesight prescription of the user to generate eyewear suitable to the user by eyewear manufacturer(s) or retailer(s).

Advantageously, in embodiments of the system 1000, which include the manufacturing file generator 106, the manufacturing specification file may be produced and provided to the manufacturer directly from the system 1000. This however requires receiving input from the user indicative of his eyesight prescription and/or indicative of his face structure.

As described in more details below, the user's input regarding his eyesight (e.g. prescription) is important for determining the manufacturing properties of the lenses of the eyewear. The manufacturing specification file includes lens manufacturing data which incorporates certain parameters which are determined based on the user's behavioral indices. For instance, according to some embodiments of the present invention the following parameters of certain lens types, such as progressive addition lenses, may be determined by the eyewear specification generator 103 without intervention/input from the user: locations and sizes of the Far Zone, Intermediate/Transition Zone, Near Zone size, and the corridor between them, as well as the desired lens material (e.g. refractive index and/or strengths thereof). Additionally, the manufacturing specification file includes lens manufacturing data which incorporates certain parameters associated with the user's eyesight, such as: Far and Near optical powers of the lens and astigmatism. In some embodiments, the manufacturing specification file also includes data which is determined based on the face structure (e.g. the interpupillary distance of the user and the height of his noise bridge) and possibly also on the eyewear frame type (which may also be a part of the eyewear specification generator). This may include for example the lens cut specification which should match both the frame type and the user's face structure.

Thus, according to some embodiments, the user interface module UI is configured and operable to utilize the mobile device 1010 for obtaining user's input regarding his eyesight prescription. The user interface module UI may be adapted to present the user with data filling form at which he should fill the details of his eyesight prescription. Alternative or additionally, the user interface module UI may be adapted to instruct the user to provide an image of his eyesight prescription sheet, and operate an OCR module (not specifically shown) to analyze the image and determine the eyesight prescription parameters therefrom. The image may be for example provided by instructing the user to operate the camera 100 of the user's device 1010 to capture an image his prescription sheet.

Additionally or alternatively, according to some embodiments of the invention the face structure of the user may also be obtained as input from the user. For instance, in some embodiments the user interface module UI is configured and operable to utilize the mobile device 1010 for obtaining user's input regarding his eyesight prescription. The user interface module UI may be adapted to instruct the user to provide/capture an image of his face. The system 1000 may include image processing face recognition/analyzing module (not specifically shown) that is configured and operable to identify facial properties of the user from the image Optionally, the system 1000 further includes a communication manager (not shown), in communication with the eyewear specification generator 103, the manufacturing file generator 106, or both the specification generator 103 and the manufacturing file generator 106. The communication manager communicates information based on the generated eyewear specification—say the file generated by the manufacturing file generator 106, to a remote party—say to a remote manufacturer's computer in control of an eyewear (say lenses) manufacturing machine, as described in further detail hereinbelow.

It should be noted that each one of parts/modules 210, 101, 102, 103, 105, 106 and 210 may be implemented as a software component (e.g. computer executable/application) or as hardware component or combination of both software and hardware. Optionally, the software components include computer application(s) installable in a mobile device (e.g. smartphone or tablet application, and/or application of smart wearable garments (e.g. smart glasses), such as an iPhone® App) which may be downloaded to, and run on the user's mobile device, say from an Application store such as the Apple® App Store. Alternatively or additionally, the software components include a server computer application which runs on a server computer, or rather a combination of the server application and the mobile application, etc., as described in further detail hereinbelow. Optionally, the computer application is run upon one or more predefined events, as described in further detail hereinbelow. Alternatively or additionally, the computer application's is run on a periodic basis, say every five minutes. In some embodiments the modules of the system which are running on a mobile device are periodically executed by the mobile device every predefined time period (e.g. several minutes)

In embodiments in which the system is configured as a distributed system of which part 1001 is implemented on the mobile device 1010 and part 1002 is implemented on the server 1020, the server part 1001 includes a data receiver 210 adapted to receive data generated from values measured using one or more sensors 100.1 carried by a user, as described in further detail hereinabove and below. Optionally, the data receiver 210 further records the received data in one or more logs.

The eyewear specification generated by the present invention may include but is not limited to one or more features which the user's eyewear (say a pair of glasses to be manufactured or assembled for the specific user) is to have, as described in further detail hereinbelow. For example, the eyewear specification may specify types of coating to be applied to lenses, materials (say types of glass of plastic to be used for manufacturing the lenses), etc., as per user needs automatically learnt from the values measured by the sensors, as described in further detail hereinbelow.

Figure 2A:
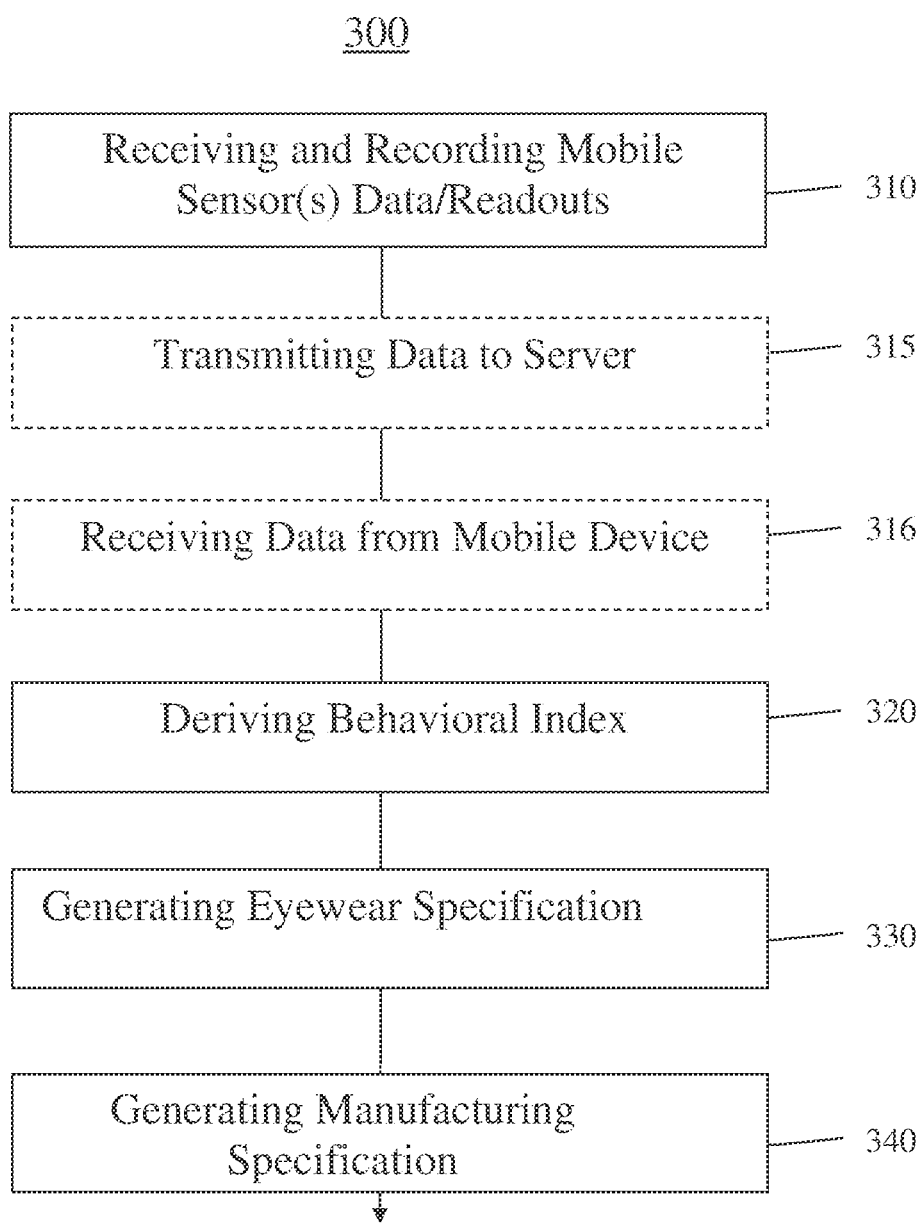
FIG. 2A is a flowchart schematically illustrating an exemplary method for automatic eyewear measurement and specification, according to an exemplary embodiment of the present invention.
Figure 2B:
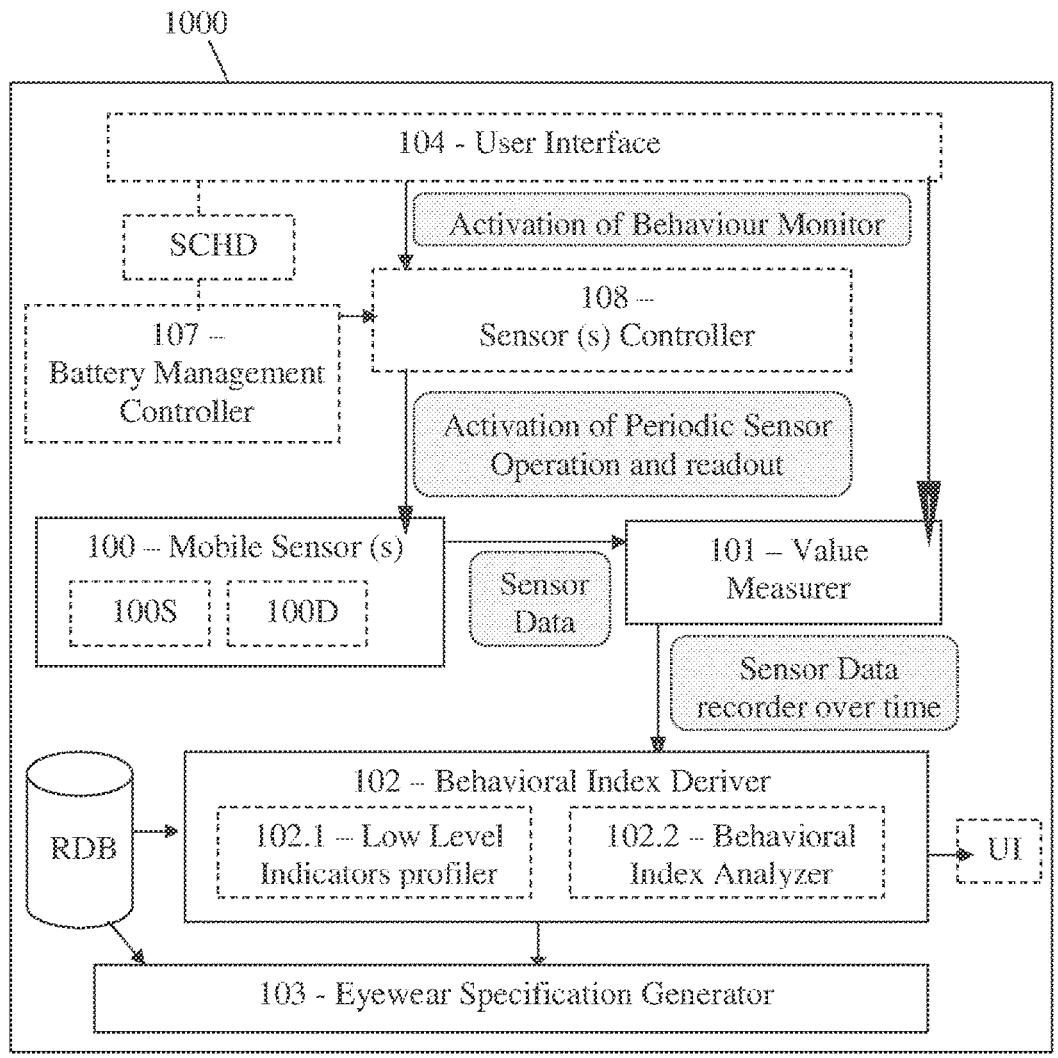
FIG. 2B is a block diagram schematically illustrating another exemplary system for automatic eyewear measurement and specification, according to an embodiment of the present invention.

Reference is now made together to FIGS. 2A and 2B, which are respectively a flowchart schematically illustrating an exemplary method 300 for automatic eyewear measurement and specification and a block diagram of an exemplary system 1000 according to an exemplary embodiment of the present invention.

The exemplary method 300 for automatic eyewear measurement and specification, according to this exemplary embodiment, may be executed by one or more computer processors of one or more devices. Each one of the devices includes one or more of the computer processors. The exemplary method may thus be executed, for example, on a mobile device such as a smart phone, a tablet computer or a user wearable device (say a smart watch), on a stationary device such as a server computer, etc., or on any combination thereof, as described in further detail hereinbelow.

In a first example, the exemplary method 300 is executed by a computer application such as an iPhone® App, which application may be downloaded to the user's smart cellular phone (say an Apple® iPhone or a Samsung® Galaxy cellular phone), tablet computer (say an Apple® iPad), etc., as described in further detail hereinabove.

In a second example, the exemplary method 300 is executed by a computer application which runs on a server computer. In the second example, the server computer is in remote communication with sensors carried by a user or with a device which samples sensors carried by a user—say with the user's smart phone, tablet computer, etc., as described in further detail hereinabove.

In a third example, the exemplary method 300 is distributed over two or more devices—say between the user's mobile device and the server computer, such that different operations of the method are carried out on different ones of the devices and implemented by different modules of the system 1000 distributed among these devices. Optionally, the distribution may be static—say with each operation being executed on a specific one of the devices only. Alternatively or additionally, the distribution may be dynamic—say with one of the operations being executed on the server computer when in communication with the user's mobile device, and on the mobile device itself when not in communication with the server computer.

In operation 310 of the exemplary method, sensor data/readout-information (values measured using one or more mobile sensors carried by the user) is received from the sensors 100 during a not necessarily consecutive period of one or more hours, days, weeks, etc'. The data may be received by the value measurer mode 101 of system 1000.

The mobile sensors 100 may include for example, one or more sensors installed on the mobile device itself (say sensors as commonly installed on a modern smart phone such as an Apple iPhone™), one or more sensors worn by the user and connected to the device over a wired or a wireless connection, etc., or any combination thereof, as describe in further detail hereinabove.

The sensors 100 may include, but are not limited a GPS (Global Positioning System) receiver, an accelerometer, a photometer, a camera, a compass, a clock, a Wi-Fi communications card, a cellular telephony 3G, 4G, or LTE communications card, etc., as described in further detail hereinbelow.

Optionally, one or more of the measured values pertains to the user's movement, as described in further detail hereinbelow. Optionally, one or more of the measured values pertains to the user's environment, as described in further detail hereinabove. Optionally, the method further includes measuring the values using the sensors 100 carried by the user—say by the value measurer 101 of apparatus 1000, as described in further detail herein above and below. Typically the value measurer resides on a mobile device of the user which includes or is in close proximity and in communication with the sensors 100.

Figure 2C:
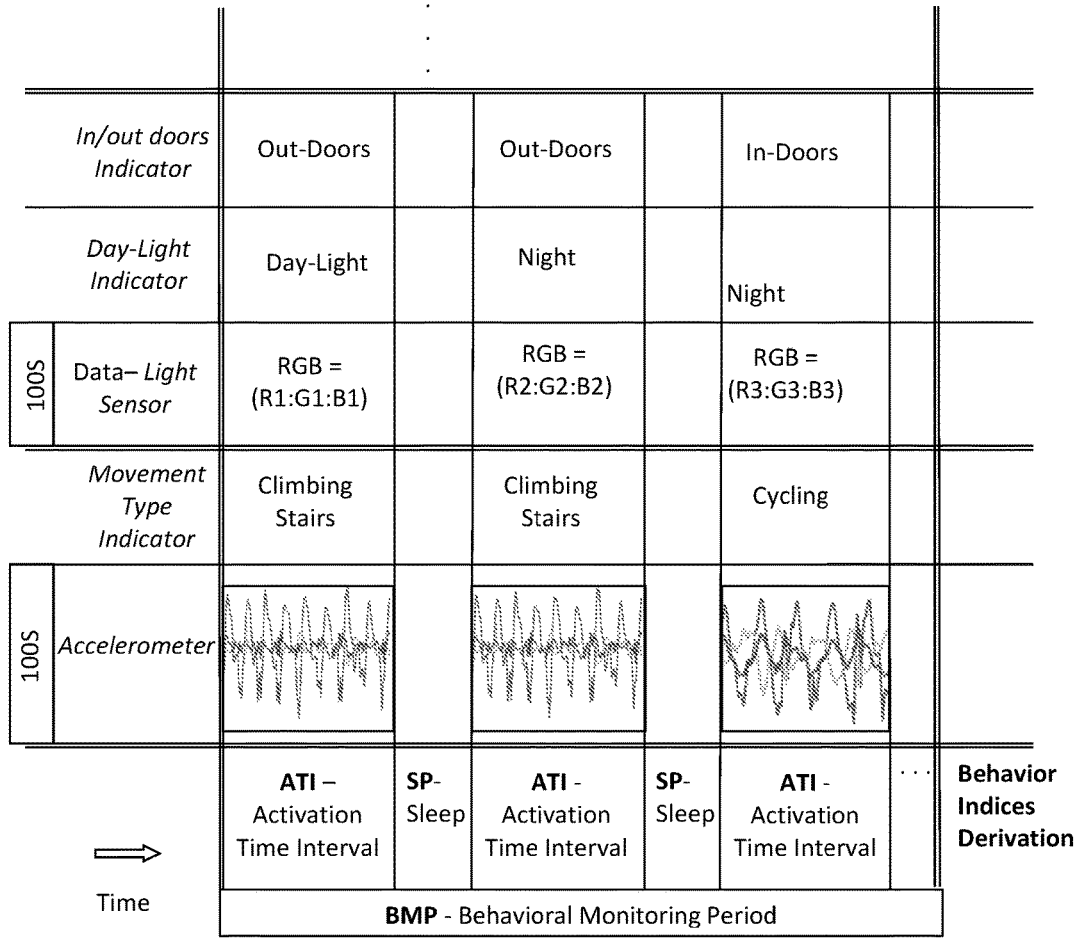
FIG. 2C is a table exemplifying data obtained from certain sensors of the a mobile device of a user in several sensor activation time intervals during a user's behavior monitoring period.

Referring now also to FIG. 2C, it is noted that as indicated above, the period BMP, during which behavior monitoring is conducted by acquiring and analyzing the data from the sensors 101 to determine the behavioral characteristics (indices) of the user. According to some embodiments of the present invention the behavioral monitoring period may be in the range from few hours to typically few days or several weeks or months. This is in order for the system 1000 to be able to acquired sufficient sensor data for statistically determining the average/typical daily behavior of the user, the average/nominal lighting and weather conditions to which he is exposed and the activities he is typically engaged with. However, sensors' 100 operation is generally energetically costly and continuous operation thereof may drain the battery of the mobile device 100 relatively quickly (e.g. within couple of hours). Therefore there is a need to limit the accumulated operation time of the sensors 100 during the behavioral monitoring period BMP. This is achieved according to the present invention by operating the sensors 100 (or at least the mobile sensors 100.1) to provide/measure data only during interleaved activation time intervals ATIs separated by sleep periods SPs at which the sensors are not activated or shut down by the system 1000. To this end according to some embodiments in order to save battery, the system 1000 includes a is an event listener module (not specifically shown in the figure), that is configured and operable issuing a triggering signal upon occurrence of one or more predetermined events (e.g. detection movement in the accelerometer) and in response initiates a measuring activation time interval ATI during which one or more of the sensors are activated and read.

As illustrated in the FIG. 2B, the system 1000 may optionally include a battery management module 107, which may be associated with a time scheduler (e.g. SCHD), and which is configured and operable for issuing trigger signals, in a timely manner, for activating the sensors 100 in time intervals ATIs during the behavioral monitoring period BMP. The system may also include a sensors' controller module 108 adapted for receiving the trigger signal from the scheduler SCHD or from the battery management module 107 and in response thereto operate/activate the sensors to operate during time intervals ATIs of predetermined durations, which are separated by sleep periods SPs. For instance the sensors 100 may be operated/activated periodically every five or ten minutes to sample the behavior/weather/environment the user is experiencing.

According to some embodiments of the present invention the duration of the activation time intervals ATIs may differ for different sensor categories. For instance, the system 1000 may include or be associated with sensors categorized in two general categories as specified below: time stationary sensors 100S and time dynamic sensors 100D. The sensors, which are referred to herein for brevity Time stationary sensors 100S, are sensors from which single sample measurement taken during an activation time interval ATI provides meaningful behavioral information about the user during the respective activation interval ATI. The time stationary sensors 100S may include for example lighting sensors, positioning sensors, temperature sensors, location, weather and/or lighting data services RDS and the like. To this end, the sensors' controller module 108 may be adapted to operate/activate the time stationary sensors 100S once (or few times) in at every time interval ATI, and the value measurer 101 may be adapted to sample (obtain the measured value of) the time stationary sensors 100S once (or few times) in at every time interval ATI, so as to take at least a snapshot (a single temporal value of the measurement obtained thereby) at the respective time intervals. Other sensors, which are referred to herein for brevity as time-dynamic sensors 100D, are sensors which should be sampled over a certain time duration (for example several second or several tens of seconds) during each activation time interval in order to obtain meaningful behavioral information therefrom. The time-dynamic sensors 100D may for example include the sensors from which the nature (e.g. type) of the movement of the user (or his mobile device) can be derived. These may include for example the accelerometer sensor, orientation sensors, rotation rate sensor and the like. Thus according to some embodiments of the invention the sensors' controller module 108 may be adapted to operate/activate the time dynamic sensors 100D over a certain extended time duration at every activation time interval ATI, and the value measurer 101 is adapted to sample (obtain the measured time sequence of values of) the time dynamic sensors 100D over the certain extended time duration at every activation time interval ATI. Accordingly during the activation time interval ATI a time sequence readings/measurements of the time dynamic sensor's 100D is obtained.

Optionally, some of the values are measured by sampling a specific one of the sensors whenever a pre-defined change occurs in values continuously or periodically measured using a predefined, other one of the sensors.

Optionally, the measured values are recorded in one or more logs, say by the value measurer 101 of system 1000.

FIG. 2C exemplifies the data obtained by the value measurer 101 from two types of sensors, accelerometer sensor and lighting sensor, belonging respectively to the time stationary and time dynamic sensor categories. As exemplified in the figure for each activation time interval ATI the value measurer 101 obtains and possibly records a single temporal measurement of the time stationary sensors (in this example the RGB lighting values (R1:G1:B1), (R2:G2:B2) (R3:G3:B3) are respectively obtained during three activation time intervals ATIs based on the user's location at these time intervals (from remote lighting data services RDS). Also exemplified in the figure is that for each activation time interval ATI the value measurer 101 obtains and possibly records a time profile of values measured by the time dynamic sensors (in this example the accelerometer measurement time profiles which are obtained from the accelerometer are graphically illustrated in the three activation time intervals ATIs).

In this regards it should be noted that in some embodiments of the present invention the value measurer 101 may be adapted for applying preprocessing to the measured/readout data obtained from the sensors. For instance, in case the light sensor is actually a camera of the mobile device 1010, the value measurer 101 may be adapted to obtain an image captured from the camera and apply image processing to the image to determine RGB values characterizing the white balance in the captured image from which certain lighting conditions to which the camera is exposed can be determined, White balance processing of the image can be performed according to any suitable white balance derivation technique/method as will be appreciated by those versed in the art of image processing.

Turning back to FIGS. 2A and 2B, in operation 320 of the exemplary method behavioral indices/characteristics indicative of the user's habits and behavior, and in particularly behavioral indices relating to eye behavior/experience of the user are derived from the sensor measurements obtained operation 310. Operation 320 may be carried out for example by the behavioral indices deriver module 102 of the system 1000, which is connected to, or is in communication with, the value measurer 101 and adapted for receiving the sensor data collected thereby during the behavioral monitoring period BMP. Generally, the behavioral indices are determined finally at the end of, or after, the behavioral monitoring period BMP during which sensor data is collected by the value measurer.

Figure 2D:
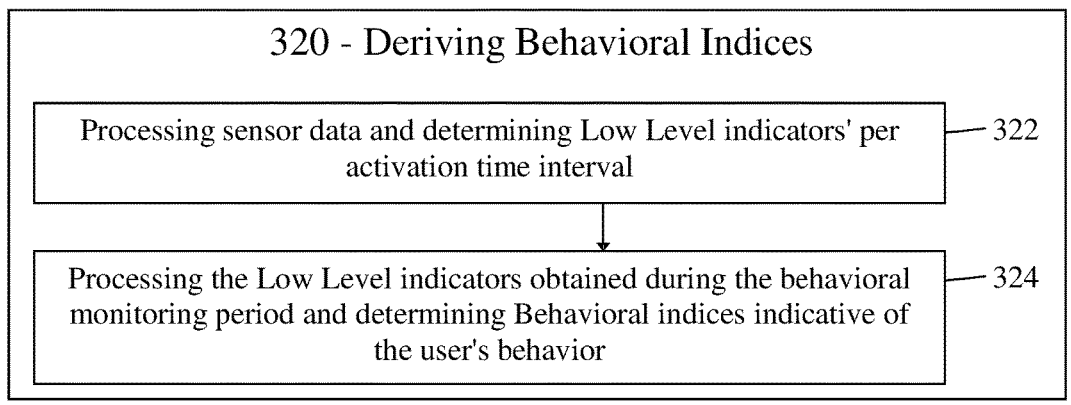
FIG. 2D is a flowchart schematically illustrating a method according to an embodiment of the present invention for processing the sensors data to derive behavioral indices characterizing the user's behavior.

As illustrated in FIG. 2D, according to certain embodiments of the present invention behavioral indices/characteristic derivation operation 320 includes two sub-operations 322 and 324.

Sub-operation 322 includes processing the sensor data obtained at each sensor activation time interval ATI and determining low level indicators' indicative of the characteristic behavior of the user during the respective time interval ATI. According to some embodiments operation 322 is performed by the Low Level Indicators profiler module 102.1, per activation time interval ATI for example during or at the end of the respective activation time interval ATI, or afterwards, or at the end of the behavioral monitoring period BMP.

Optionally, for deriving the behavioral indexes, there is further used one or more databases RDB, which may or may not be included in the system 1000, or may be associated with the system via data communication. The databases used may include but are not limited to, for example, databases accessible publically (say over the internet), private databases (say a database already embedded in the computer application), as described in further detail hereinbelow.

For example, for deriving the behavioral indexes, there may be used one or more of the weather, UV radiation exposure, temperature, and other databases currently available from government agencies and other entities (say universities or private firms), as described in further detail hereinbelow. To this end, as specified in more details below, the term sensors 100 may optionally also referred to herein as a so called Data-Provider module (see 100.2 in FIG. 3A) which may be a communication module configured and operable for communication with certain specified databases/repositories RDB via a data network to provide measured data indicative of various weather/environmental conditions which may affect the user during the behavioral monitoring period. Optionally, for deriving the behavioral indexes, there is further used one or more history databases. In one example, for deriving the behavioral indexes, there is further used a database of historic values previously measured by one or more of the sensors, a database of historic data obtained from the weather, UV radiation exposure, temperature, or other databases, etc. as described in further detail hereinbelow.

Optionally, the derived behavioral indexes are recorded in one or more logs, say by the behavioral index deriver 102 of system 1000 or the behavioral index deriver 102 of apparatus 1000, as described in further detail hereinabove.

Sub-operation 324 includes processing the Low Level indicators obtained during the behavioral monitoring period BMP and determining Behavioral indices/characteristics characterizing the user's behavior during the behavioral monitoring period BMP or a part thereof. According to some embodiments operation 324 is performed by the Behavioral Index determination module 102.2, during of the behavioral monitoring period BMP, at the end of the behavioral monitoring period BMP or afterwards. Operation 324 may include various processing applied to the lower level indicators obtained for the period BMP to determine average/nominal behavioral indices characterizing certain aspects of the user's behavior, and in particular aspects associated with user's use of his eyes, and the lighting and weather affecting that use. This may be based on any suitable function of the low level indicators obtained for the plurality of time intervals (e.g. by averaging the values obtained from one or more low level indicators over the plurality of time intervals). For instance the lighting conditions indicators may be processed to determine the UV exposure blue light exposure, sun-glare to which the user is exposed during each time interval ATI and these may be further averaged over the behavioral monitoring time to determine behavioral indices indicative of the nominal exposure of the user to UV, blue/HEV light and/or sun glare. Alternatively or additionally in some cases the system includes or is associated with a database RDB including reference data associating the various values of the low level indices with a characterizing values of behavioral parameters. For instance low level indices indicative of user movement types such as running, cycling, reading, climbing stairs and others may be associated in the database with various eye-gaze direction properties, focusing distances of the eyes, viewing angles of the user and more. In operation 324 the Behavioral Index Computer module 102.2 may be adapted to access the reference data database RDB to determine the behavioral parameters associated with the values of certain low-level indices (e.g. the behavioral parameters associated with movement type low level indices) determined for one or more time intervals ATIs during the behavioral monitoring period BMP. Then the Behavioral Index Computer module 102.2, determines behavioral indices indicative of these behavioral parameters during the behavioral monitoring period BMP, for instance by averaging the behavioral parameters determined for the various ATIs of the behavioral period.

In a second example, the received 310 data already includes one or more behavioral indexes which pertain to the user and are derived using the measured values, say by a device in use by the user (say a smart mobile phone), as described in further detail hereinabove.

Optionally, the behavioral indexes, which pertain to the user, are presented to the user in a User Interface UI, say on a screen of the user's smart cellular phone—say by the GUI manager of the mobile device 1010 or of the system 1000. Optionally, the GUI Manager represents the behavioral indexes through an interactive GUI. The GUI Manager may update content presented on the GUI continuously, or rather once in a predefined time period (say every ten minutes), or per a triggering of the user when clicking on one of the GUI's buttons or a remote triggering by communication from a remote server, etc., as known in the art.

Further in the method, there is generated 330 an eyewear specification for the user.

The eyewear specification includes, but is not limited to data about one or more features, as described in further detail hereinbelow, which the user's eyewear (say a pair of glasses to be manufactured or assembled for the specific user) should have in order to meets the user expressed by the behavioral indices derived in operation 320.

For example, the eyewear specification may specify types of coating to be applied to lenses, materials (say types of glass or plastic to be used for manufacturing lenses for the user's eyewear), etc., as per the user's needs as automatically learnt from the values measured using the sensors, as described in further detail hereinbelow.

Optionally, according to the present invention the eyewear specification is generated 330 based on passive learning of the user's needs from the user's behavior indices/characteristics obtained through a behavioral monitoring time period BMP during which the sensors' 100 values are measured, say through one or more of the user's day or through a number of hours. Optionally, the eyewear specification is generated 330 from behavioral indexes derived from the values measured using the one or more sensor(s) when being carried by the user (say for one or more days), as described in further detail hereinbelow. Operation 330 may be for example carried out by an Eyewear Specification Generator module 103 of the system 1000.

Optionally, for generating 330 the eyewear specification, there is further used one or more reference databases RDB. These for clarity are indicated by the same reference numeral RDB as the reference database which is described above with relation to operation 320.2. The databases RDB may include but are not limited to, for example, databases accessible publically (say over the internet), private databases (say a specific optical vendor's database already embedded in the computer application, which database may also be updated periodically by the application), etc., as described in further detail hereinbelow. The databases RDB may be connected or associated with the Eyewear Specification Generator module 103 via data communication optionally over a data network. Optionally, in operation 330 the Eyewear Specification Generator module 103 utilizes the behavioral indices obtained in operation 320 to query the reference databases RDB for finding reference eyewear specification parameters matching the user's behavior as characterized by the behavioral indices.

For instance, as will be described further below, the reference databases RDB may include an optical coating ant filters data base associating the values of various lighting behavioral indices with required/recommended lens coatings and/or filters to be included in the eyewear specification generated in 330. Optionally, in operation 330 the Eyewear Specification Generator module 103 utilizes the lighting behavioral indices obtained in operation 320 to query the reference databases RDB to determine eyewear coatings and/or filters matching the lighting behavioral indices of the user.

Alternatively or additionally the reference databases RDB may include eyewear frame types' data base including reference data associating the values of various types of the user activities or various combinations of the user activities with recommended eyewear/eyeglasses frames. Optionally, in operation 330 the Eyewear Specification Generator module 103 utilizes activity type behavioral indices obtained in operation 320 to query the reference eyewear frame types database RDB to determine eyewear frame types matching the activity type behavioral indices which are indicative of the activities with which the user is typically engaged.

Alternatively or additionally the reference databases RDB may include an optical lens design database including data indicative of various lens designs (for example various designs of progressive addition lenses (PAL lenses) suitable for various activities or combination of activities of the user. Optionally, in operation 330 the Eyewear Specification Generator module 103 utilizes activity type behavioral indices obtained in operation 320 to query the reference optical lens design database RDB to determine an optical lens design types matching the activity type behavioral indices of the user.

Alternatively, the Eyewear Specification Generator module 103 also includes custom optical lens design generator which is capable of generating optical lens design specification which is custom made and designed as per the user's behavioral characteristics/indices obtained in 320.

Alternatively or additionally the reference databases RDB may include lens material data base including data indicative of various materials used for lenses, their optical properties (e.g. refractive indices), their physical properties (strengths/durability), and/or their thermal properties. Optionally, in operation 330 the Eyewear Specification Generator module 103 utilizes activity and possibly also weather behavioral indices indicative of the user's typical activities and the weather at which they are performed to query the lens material reference data base RDB to determine lens material suitable for the user's typical activities and the weather at which he performs these activities. For instance high refractive index materials which yield thinner lenses provide elegant look suitable for office/business activities. However in some cases these materials are breakable more easily and are therefore less suitable for sport activities. Alternatively or additionally the thermal properties of glass materials may be preferred in cases in which the user is exposed to foggy weather conditions (e.g. a combination of high humidity and varying temperatures) than plastic ones.

As indicated above the operations required for generating the eyewear specification (e.g. operations 310, 320 and 330) may be passive operations which are carried out by the system 1000 without requiring or requesting any input data or engagement from the user. Optionally, however in some embodiments of the present invention after operation 330 the method proceeds to optional operation 340 for generating a manufacturing eyewear specification for the user's eyewear based on the eyewear specification provided in operation 330. To this end, in some embodiments the method includes communicating the eyewear specification, which is automatically obtained by the system in 330, to a $3^{rd}$ party by which operation 340 can be carried out to determine the eyewear manufacturing specification (e.g. the $3^{rd}$ party may be a point of sell (POS) of eyewear). Here there may be further generated a file in a predefined manufacturing machine readable format, based at least on the generated 330 eyewear specification, say by the file generator 106 of system 1000. However, here additional user data may be required, for instance user input data indicative of the eyesight prescription of the user and/or the face structure of the user. Typically, obtaining such data requires the user's engagement for providing it for example by using the camera of his mobile device 1010 or the UI of the user's device (e.g. by filling appropriate data from which may be presented to the user and filled by the user via appropriate data input from which is in some embodiments presented to the user by the file generator 106 via the UI (e.g. display and keyboard) of his mobile device 1010.

The eyewear manufacturing specification may then be prepared in 340 based on the eyewear specification and the user's eyesight prescription and the user's face structure and be stored in a file of an input file format used by an eyewear (say lenses) manufacturing machine, by a three dimensional (3D) printing system adapted for printing lenses (say from plastic), etc., as known in the art.

To this end it should be understood that even though the personal data (e.g. eyesight prescription and/or facial structure) may be inserted manually by the user, the eyewear specification design itself (e.g. the progressive addition lens design as well as the recommended coatings/filters, frame type etc' may be derived automatically, without any input from the user (i.e. passively) by the system 1000.

Optionally, the system 1000 is further adapted to be responsive to user input instructions for communicating information based on the generated 340 eyewear manufacturing specification (say the file of the format used by the manufacturing machine) to a remote party (e.g. to a remote manufacturer's computer in control of the manufacturing machine). For example, the information may be communicated by the communication manager of apparatus 1000, as described in further detail hereinbelow.

As indicated above optionally the system 1000 is distributed among the client's/user's mobile device 1010 and a remove server system 1020. Generally, the sensor data is obtained by the value measurer 101 from the sensors of user's mobile device 1010 or from sensors connected thereto by wired or wireless communication, while the behavioral index deriver may reside at the mobile device 1010 or at the remove server system 1020. In the latter case, method 300 further includes operations respective optional operations 315 and 316 in which the data collected from the sensors by the value measurer 101 is communicated (operation 315) from the mobile device 1010 by the sub-system 1001 residing thereat and respectively received (operation 316) by the remote server system 1020 by the sub-system 1002 residing thereat. This allows the rest of the method operations 320, 330, and optionally 340, to be carried out at the server side.

Figure 3A:
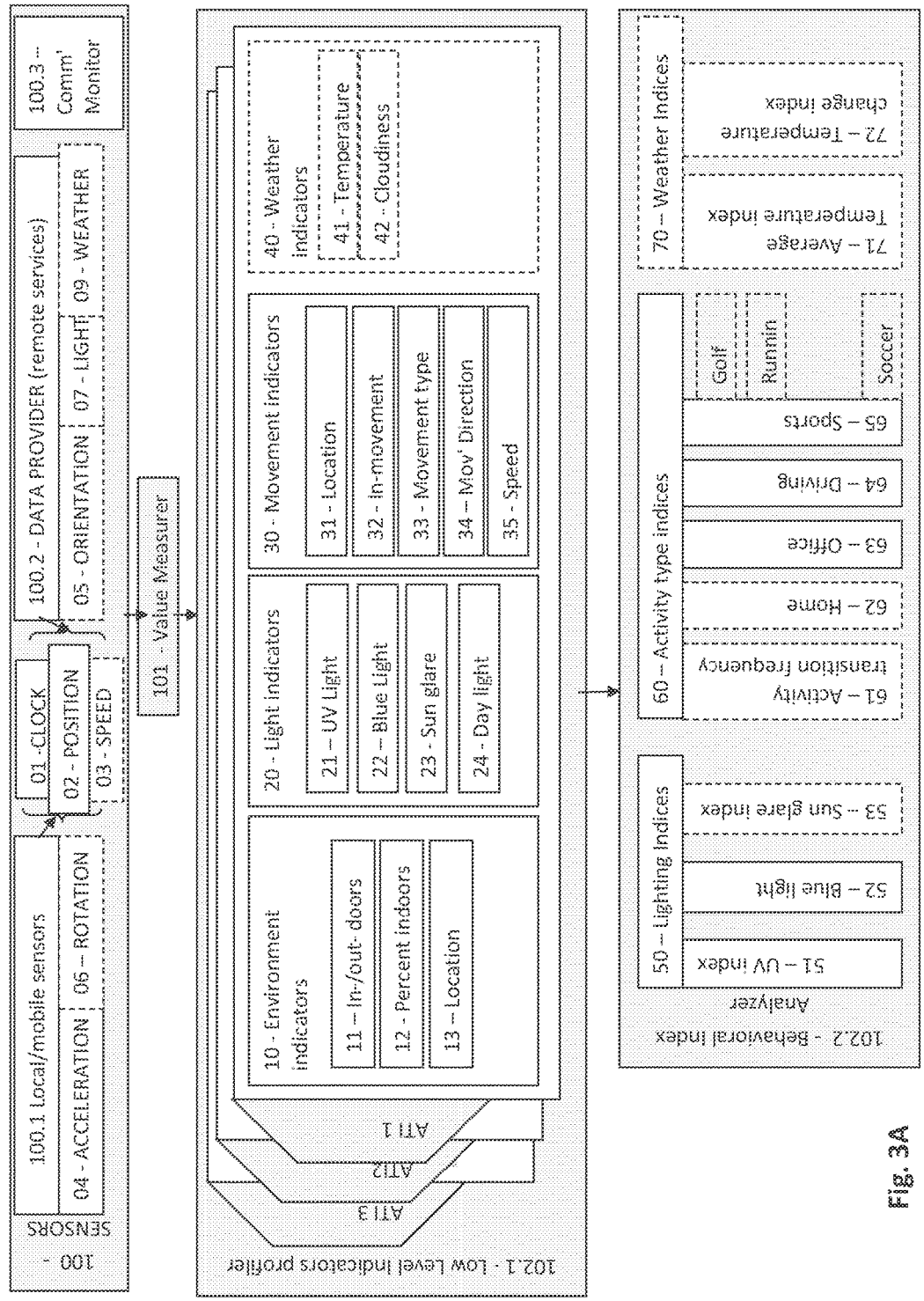
FIGS. 3A and 3B are block diagrams schematically illustrating an operation of a system for automatic eyewear measurement and specification according to an exemplary embodiments of the present invention, whereby
Figure 3B:
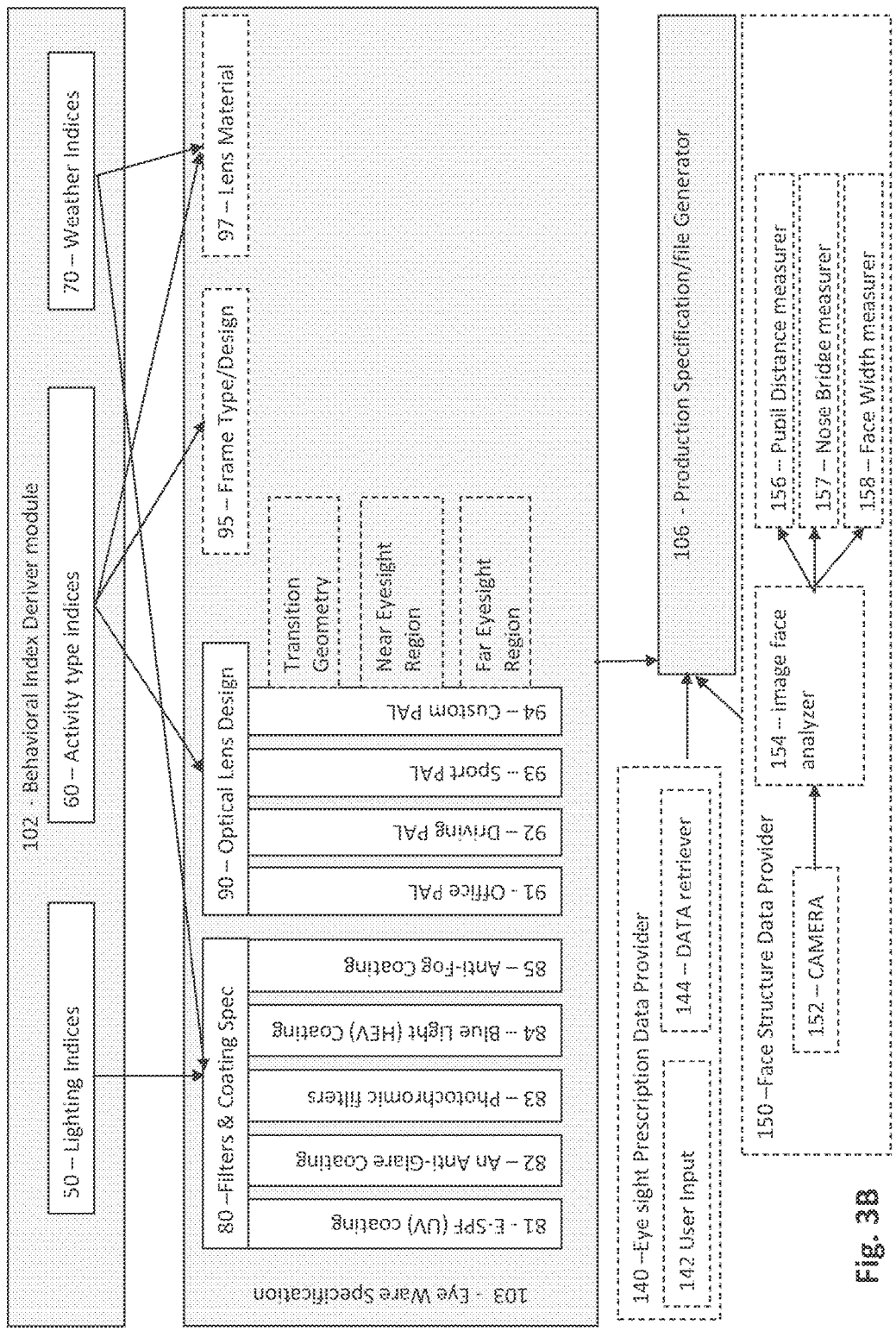
Figure 4A:
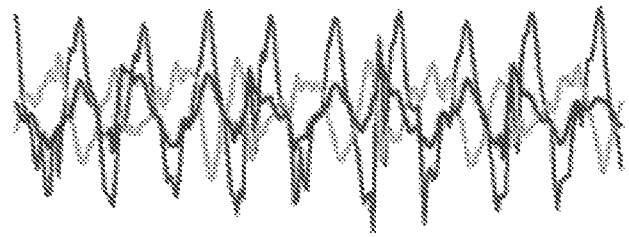
FIGS. 4A to 4D are four simplified diagrams graphically illustrating accelerometer signals related to different activity types, according to an exemplary embodiment of the present invention.
Figure 4B:
Figure 4C:
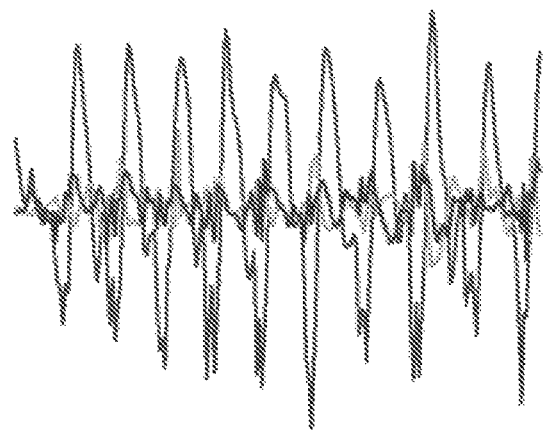
Figure 4D:

Reference is made not together to FIGS. 3A and 3B which show in more details how the operations 310 to 340 of method 300 are implemented in a specific and non-limiting embodiment of the present invention.

In this particular example the set of sensors 100 which are used in method 300 to monitor the user's behavior include three groups/types of sensors as follows:

Group I: Sensors 100.1 which are local to the mobile device 1010 of the user (namely mobile sensors). In the present non limiting example these includes the motions sensors (e.g. at least an accelerometer 04 but possibly also rotation rate sensor (e.g. Gyro) 06, an orientation (compass) sensor 05), by which user movements can be measured/estimated. In this example also the positioning sensor is a local GPS receiver. Indeed in some embodiments the local sensors 100.1 may also include other types of sensors such as weather, lighting, however in some cases such information is obtained more reliably from remote data services RDS based on the user location.

Group II: Data provider 100.2 which is connectable to remote data services RDS by which in the present example sensor data 07 and 09 indicative of the lighting and weather conditions to which the user is exposed is respectively obtained based on the location of the user.

Group III: Communication monitor(s) 100.3 which is/are adapted to monitor the communication modules WCC of the mobile device 1010 (e.g. the WiFi and/or Bluetooth and/or cellular communication modules, and/or the GPS receiver WCC) and thereby determine the environment (in-/outdoors) at which the user is located (e.g. based on the state/communication properties/gateways to which these communication modules are located). The communication monitors may be adapted to determine the strengths of received signals (e.g. radio frequency (RF) signals) from one or more WiFi/BT/Cellular/GPS signal sources and thereby determine/estimate if the user is indoors or outdoors.

Thus in the present example the sensors optionally include the following:

01—Clock: providing date/time information—this may be a local mobile sensor;

02—Positioning sensor and/or 03—speed sensor: this may be a GPS or other positioning module as may be known in the art which is capable of obtaining position and/or speed information relating to the user's mobile device (e.g. based on network location and/or inertial measurements or any other technique), and/or a connection to a remote location data services providing such information about the mobile device of the user 04—Accelerometer sensor: a sensor capable of measuring the acceleration of the user's mobile device relative to one or more spatial axes of measurement;

05—Orientation sensor and/or 06—Rotation-rate sensor: the may be a compass a gyro and/or any known in the art sensor from which the orientation and/or rotation rate (the change in the orientation of the user's mobile device) of the user's mobile device 1010 can be determined;

07—light sensor: this may include a connection to a remote data service (via the data provider 100.2) providing lighting conditions information or a suitable mobile optical sensor (e.g. a light sensor installed on smart wearable garments that are typically exposed to the environment), by which the lighting conditions to which the user is exposed can be determined.

09—weather/temperature sensor: this may include a connection to e remote data service providing weather condition (via the data provider 100.2) or a suitable mobile sensor adapted for measuring weather properties such as temperature or humidity.

100.2 the Data Provided: this may a communication module which is configurable for accessing one or more predetermined remote data services (e.g. data repositories, databases and/or websites) from which various data such as lighting, weather and/or other environmental information can be determined for the location/position of the user (of his mobile device).

It should be understood that the list of sensors is provided above only as a none-limiting example of the sensors 100 which typically exist in mobile devices and which may be used by the system 1000 to determine the user's behavior characteristics. It should also be understood that the system may be configured and operable with various types of mobile devices having possibly different sensor specification. The value measurer 101 may be adapted to interrogate the mobile device to determine the specification/listing of sensors included therein, and obtain the sensors data accordingly. In turn, per each specific the behavioral index to be determined by the system, the behavioral index deriver 102 may be include several processing routings allowing it to determine the behavioral index based on different combinations of sensors. For instance lighting condition indices may be derived by two example routings:

Routine 1: utilizing lighting conditions data measured by the light module 07;

Routine 2: determining whether the user is in-doors or outdoors, and utilizing the data provider 100.2 to obtain weather information indicative of the outdoors lighting condition, and possibly using an estimated reference data indicative of indoors lighting conditions.

To this end, the behavioral index deriver 102 may be configured and operable to select the routines to be used for determining each particular behavioral index based on the sensor types and/or based in the availability of various sensor data from the user's mobile device 1010. In this regards, the below exemplified routings for obtaining the behavioral indices should not be considered limiting and are provided only to exemplify the possible routines for deriving certain behavioral indices based on the sensors 01-09 listed above.

As indicated above, optionally, the derivation of the behavioral indexes which pertain to the user from the values measured using the mobile sensors, involves a calculation of one or more low level indicators from the measured values and a calculation of the behavioral indexes from those calculated lower level indicators.

Optionally, the calculation of the lower level indicators and the calculation of the behavioral indexes are carried out by respective modules 102.1 and 102.2 of the behavioral index deriver 102 of system 1000 as described in further detail hereinabove.

The calculation of the lower level indicators may be based on the values measured using the sensors 100 (say by reading the values from the logs), on one or more of the databases mention hereinabove and hereinbelow, on Artificial Intelligence (AI), on Heuristic Methods/routines, on Statistical Methods/routines, etc., as may be known in the art.

Optionally, as indicated above, each one of the lower level indicators may be calculated per each predefined time frame/interval (or rather per a predefined number of sensor measurements) within the time period/interval of the measuring of the values (i.e. a time segment within that time period), say to a time interval of five minutes. For instance in this figure it shows that the calculated lower level indicators are optionally calculated as per each of the activation time intervals ATI1 to ATI3.

Optionally, the lower level indicator's value for each time frame is recorded in a log/database/storage, say by the behavioral index deriver of system 1000, as described in further detail hereinabove.

Typically, as also illustrated in the figure, the low level indicators which are computed/determined by the system 1000 may be classified to for main classes of indicators determined by sub-modules 10, 20, 30 and 40 of the behavioral index deriver 102 (e.g. sub modules of module 102.1 thereof), as follows:

I. Environment indicators are determined by the environment indicator module 10 and are indicative of the user being at an indoors or outdoors environment at one or more time interval/frame ATI during the behavioral monitoring period BMP;

II. Lighting indicators are determined by the lighting indicator module 20 and are indicative of the lighting conditions to which the user is exposed during one or more time interval/frame ATI of the behavioral monitoring period BMP;

III. Movement indicators are determined by the Movement indicator module 30 and are indicative of activity type with which the user is engaged during one or more time interval/frame ATI of the behavioral monitoring period BMP; and IV. Weather indicators are determined by the Weather indicator module 40 and are indicative of the weather conditions to which the user is exposed during one or more time interval/frame ATI of the behavioral monitoring period BMP.

In the following provided is a none limiting list of optional low level indicators which may be determined by the behavioral index deriver 102 (e.g. by module 102.1 or sub-modules thereof), in conjunction with the optional sub modules 10-40 used to derive them and one or more example routines/methods which may be executed by these respective modules to determine the values of each of these low level indicators form the sensor data obtained by the value measurer 101. Thus the list of indicators modules may optionally include, but is not limited to any one or more of the following:

I. Environment Indicator Module 10

The environment indicator module 10 is configured and operable to carry out the methods described in the following in order to determine the time/frequency the user spends indoors and/or outdoors. The environment indicator module may include for example the sub-modules:

1) An indoors/outdoors indicator module 11 adapted to determine an indication on the user's spending a significant part of the user's time indoors or rather outdoors.

Optionally, the indoors/outdoors indicator 11 is calculated using values measured using a sensor such as a GPS receiver, a Wi-Fi communications card, a cellular communications card, a BlueTooth communications card, etc., or any combination thereof, on the user's mobile device 1010.

In a first example of a method/routing to determine the indoors/outdoors indicator, the behavioral index deriver 102 (e.g. module 11) determines that the user spends his time indoors when for a predefined time frame, no or poor GPS signal is received by the GPS receiver 02 or when during that time period, all received GPS signals originate with a same single satellite.

Similarly, in a second example or a method/routing to determine the indoors/outdoors indicator 11, the behavioral index deriver 102 (e.g. module 11) determines that the user spends his time indoors when all values measured by the Wi-Fi communications card for the predefined time frame indicate that the user's mobile device is connected to a wireless Wi-Fi network and/or if it gets a strong WIFI signal (e.g. higher than a certain predetermined threshold value which on high probability indicates that the user is indoors or located in the vicinity to a building).

In a third example of a method/routing to determine the Indoors/outdoors indicator 11, the behavioral index deriver 102 (e.g. module 11) determines that the user spends his time outdoors when GPS signals are received by the GPS receiver from at least two satellites or when the received GPS signal is strong (with intensity higher than a certain predetermined threshold).

Similarly, in a fourth example of a method/routine, the behavioral index deriver 102 (e.g. module 11) determines the Indoors/outdoors indicator indicates that the user spends his time outdoors when all values measured using the Wi-Fi communications card for the predefined time frame indicate that the user's smart phone is not connected to any wireless Wi-Fi network.

In a fifth example of a method/routine, the behavioral index deriver 102 (e.g. module 11) determines that the user appears to spend some time indoors and some time outdoors during a certain time frame/interval ATI. in case during that time frame ATI, both the values measured using the GPS receiver fluctuate between zero and non-zero and the values read by the Wi-Fi communications card fluctuate between values, which indicate a connection to a wireless Wi-Fi network—say the network's SSID (Service Set Identifier) and values which indicate a lack of such a connection, as known in the art. In this way the behavioral index deriver 102 (e.g. module 1.1) may also determine the percent in-doors/out-doors indicator 12 and the location switching indicator 13 which indicate the time/ratio the user spends his time indoors/outdoors and the number of times the user switches between indoors and outdoors.

According to various embodiments of the invention the behavioral index deriver 102 (e.g. module 11 thereof) may be configured to use any one or any combination of the above methods/routines to determine whether the user is located indoors or outdoors during a particular time interval.

2) A location switching indicator module 13 is configured and operable to count of the number of times in which the user switches from being indoors to being outdoors per the time frame, say using the indoors/outdoors indicator, as described in further detail hereinabove.

3) A percent indoors indictor module 12, configured and operable to determine the percentage of user's time in which the user is present indoors.

In one example, the behavioral index deriver 102 (e.g. module 12 thereof) calculates the percent indoors indicator, by averaging or accumulating or using another predetermined function to process the indoors/outdoors indicators over time, while possibly taking into consideration the time frame/interval ATIs which each indoors/outdoors indicator refers to.

Typically, in that predetermined function (e.g. averaging or accumulation), there is given a full weight to time frames in which the indoors/outdoors indicator indicates that the user spends his time outdoors, and a fraction of that weight to time frames in which the indoors/outdoors indicator indicates that the user spends some of his time outdoors and some of his time indoors.

II. Movement Indicator Module 30:

4) A location indicator module 31 is configured and operable to process the sensors data to determine a time based indication on location of the user. The indication may include for example, the geographical coordinate values of the user's position, a name and a place type (say 'Metlife', 'Football Stadium'), etc., or any combination thereof, as described in further detail hereinbelow.

Optionally, according to one method/routing for calculating the location indicator 31, the behavioral index deriver 102 (e.g. module 31 thereof) uses the values measured by the GPS receiver 02 as well as location services such as Google® APIs on an Android Smart Phone, or IOS APIs on an Apple® iPhone or iPAD Device which may be obtained via the data provider 100.2.

Optionally, according to another method/routing for calculating the location indicator 31 for a certain time interval/frame e.g. ATI2, the behavioral index deriver 102 (e.g. module 31 thereof) further uses the indoors/outdoors indicator 11, such that when the indoors/outdoors indicator 11 indicates that the user spends his time indoors, the location indicator is set to a value similar to that of the previous time interval. However, when the indoors/outdoors indicator 11 indicates that the user spends his time outdoors or some time indoors and some time outdoors, the entry is set according to a location based on the signals received by the GPS receiver in the most recent preceding time frame/interval, e.g. ATI1, for which the location indicator 21 was determined.

5) An in-movement indicator module 32 is configured and operable to process the sensors data to determine data indicative of whether the user is moving or is rather relatively static. According to various methods/routines for calculating the in-movement indicator 32, the behavioral index deriver 102 (e.g. module 32 thereof) may utilize the values measured by any one or the following: the accelerometer 04 or the GPS/position 02 sensors, location services data obtained from the data provider 100.2, based on the value of the indoors/outdoors indicator 11, or on any combination thereof. For example the values of any one of the above listed sensors/indicators at the present time interval (e.g. ATI2) may be compared to their values at the preceding time interval (e.g. ATI1) and in case of a change the in-movement indicator 32 may be set to indicate that the user is moving.

Alternatively or additionally, according to one routine/method, when during the time frame ATI2, the indoors/outdoors indicator 11 indicates that the user spends his time indoors, the in-movement indicator 32 is calculated on basis of the values measured by the accelerometer 04.

Yet alternatively or additionally, according to another routine/method when the accelerometer 04 measured values exceed a threshold predefined (say by an administrator or programmer of system 1000), the in-movement indicator 32 is set with a value which indicates a movement. However, when the accelerometer 04 measured values do not exceed the predefined threshold, the in-movement indicator 32 is set with a value which indicates that the user is relatively static (say as the user is sitting and looking at a computer screen).

According to yet another optional routine/method, when during the time frame (e.g. ATI2), the indoors/outdoors indicators 11 or 12 indicate that the user spends at least some of his time outdoors, the in-movement indicator is calculated on basis of the presence or absence of changes in values measured by the position/GPS sensor 02.

According to various embodiments of the invention the behavioral index deriver 102 (e.g. module 32 thereof) may be configured to use any one or any combination of the above methods/routines to determine the in-movement indicator (whether the user is in movement or not).

6) A movement direction indicator module 34 may be is configured to operate in case for the respective time interval/frame (e.g. ATI2), the indoors/outdoors indicators 11 or 12 indicates that the user spends at least some of his time outdoors. The movement direction indicator module 34 is configured and operable to process the sensors data to determine an averaged direction of the user's movement during the time interval.

In one example of routine/method, the behavioral index deriver 102 (e.g. module 34 thereof) calculates the averaged direction on basis of values measured using the GPS/position receiver/sensor 02, the location services which may be provided by the data provider 100.2, or any combination thereof. This may be achieved for example by tracking the user's location as given by the location indicator 31, as described in further detail hereinabove.

7) A speed indicator module 35 is configured and operable to process the sensors data to determine an average speed of the user's movement during the time frame/interval (e.g. ATI2). According to one routing/method the behavioral index deriver 102 (e.g. module 35 thereof) may be configured to determine the user's speed on basis of values measured using the GPS/position receiver/sensor 02, the accelerometer 04, and/or any combination thereof. For instance the behavioral index deriver 102 (e.g. module 35) may be adapted to track the user's location as given by the location indicator at a present time interval ATI2 and previous or preceding time intervals.

8) A movement type indicator 33 is configured and operable to process the sensors data to determine an indication on the type of physical activity with which the user in engaged based on an analysis of the user's movements per the predefined time frame/interval (e.g. ATI1), for instance on an hourly basis (i.e. per hour) or as per few minutes. The movement type indicator 33 may indicated the user is engaged with any one of a plurality of activities such as: the user's is a static, driving, walking, running, sailing, cycling, etc.

Optionally, the behavioral index deriver (e.g. module 33 thereof) calculates the movement type indicator on basis of values measured by any one or more of the following sensors: the GPS/positioning receiver/sensor 02, the location services provided by the data provider 100.2, the accelerometer 04, the rotation rate sensor 06, the speed sensor 03 or others. In some embodiments the behavioral index deriver 102 (e.g. module 33) employs one or more routines for determining the user's activity from the data of these sensors by applying pattern recognition and/or statistical techniques such as a pre-trained Neural Network (NN) or Deep Neural Network (DNN) Model, or any combination thereof, to this data. In this regards as indicated above the data obtained for certain types of sensors, being time dynamic sensors 100D, such as the accelerometer 04 and/or the rotation rate (e.g. Gyro) sensor 06 may be time profile of the measurements taken during the respective time interval (e.g. ATI1). This time profile, possibly together with time profile(s) or snapshots of measurements obtained from additional sensors (time static 100S or time dynamic 100D sensors) may be processed by the dedicated pattern recognition or statistical techniques to classify/associate the measurements obtained during the respective time interval (e.g. ATI1) with a corresponding activity of the user. Example of calcification of certain sensor measurements to activity types is described in further detail hereinbelow, for example with reference to FIGS. 4A-4D.

Thus, in one example, for a time frame ATI of several seconds/minutes (e.g. sixty seconds), the behavioral index deriver (e.g. module 33) collects the values measured say at each one of the sixty seconds, by the GPS receiver or by the accelerometer, possibly together with the indoors/outdoors indicators for those seconds, the speed indicators for those seconds, or both.

Then, in the some embodiments, the behavioral index deriver (e.g. module 33) sends the collected values, the indicators, or both, to a classification engine (not specifically illustrated), which may be based for example on a DNN or an NN Model, as known in the art. The classification engine may be associated with, or included in, the system 1000 and may be local or remotely connectable to the system 1000 via data communication)

The classification engine determines a movement type—say a one of driving, walking, running, sailing, etc.—based on the indicators and values, and sends the determined movement type back, for the behavioral index deriver to set the Movement Type Indicator 33 with. To this end, as will be readily appreciated by those versed in the art the movement type classification can be obtained from the measurements of the motion sensors (e.g. the accelerometer and/or rotation-rate/gyro) by using a pre-trained neural network (NN or DNN) and/or deep learning techniques and/or statistical methods and/or any suitable 3rd party (e.g. based on IOs and/or Android systems) that are able to determine Motion Activity/type information automatically from the motion sensors' measurements.

III. Lighting Indicators Module 20:

The Lighting indicators module 20 is configured and operable to carry out the methods described in the following in order to determine the lighting conditions to which the user is exposed indicator module and may include for example the following sub-modules:

9) A UV indicator module 21, is configured and operable to process the sensors data to determine data indicative of the UV Radiation to which the user is exposed (e.g. according to user's geographical location(s) and whether he is indoors or outdoors), per a predefined time frame/interval ATI, and possibly also based on the time of day and/or the cloudiness indicator (i.e. percentage of cloud sky coverage) determined for each time interval ATI.

Optionally, according to one exemplary method/routine the behavioral index deriver 102 (e.g. module 21 thereof) determines/calculates the average UV indicator based on the user's location as given by the values measured by the GPS receiver 04, and/or or based on data obtained by the data provider 100.2 from the location services and/or from one of the location based UV exposure databases available to the general public over the internet—say from the AccuWeather.com® website.

Optionally, the UV exposure database which is used by the system 1000 is a one which ranks the UV exposure per geographical location (say for a specific town), say according to the internationally recognized scale of 0-14, as adopted and standardized by the UN (United Nations) World Health Organization and the World Meteorological Organization in 1994. This UV index (values from 1-14) indicates the maximal UV exposure estimated on a specific location at the respective day.

Thus, in one example, once in every time interval ATI, the behavioral index deriver (e.g. module 21) uses the in/out doors indicator to 11 to determine whether the user is outdoors and in case he is the behavioral index deriver (e.g. module 21) uses location indicator 31 and one of the UV exposure databases, to determine the UV level of exposure (say from 1 to 10) in the user's geographical location, for that hour. In case the user is indoors the behavioral index deriver sets the UV level of exposure to a predetermined value (e.g. 1 in the scale from 1 to 10 mentioned above).

Then, at the end of the behavioral index monitoring period BMP, say once in 12 hours, the behavioral index deriver 102 (e.g. module 21) calculates the UV indicator for the user's geographical location(s) during the time frame, for instance by averaging over the determined hourly UV exposure levels and/or utilizing another predetermined function of the UV exposure levels such accumulation or other statistical methods.

10) A blue light indicator module 22 is configured and operable to process the sensors data to determine the blue light exposure of the user which gives an estimate on the user's exposure to High Energy Visible Light (HEV). HEV light is high-frequency light in the violet/blue band from 400 to 500 nm, in the visible spectrum. HEV light has been implicated as a cause of retinal damages such as age-related macular degeneration. For examples, today, fluorescent lights, LED lights, and computer screens are all HEV light sources of frequent use.

Thus, in a first example, the behavioral index deriver 102 (e.g. module 22) derives the blue light personal indicator value by determining whether both the indoors/outdoors indicator 11 gives an indication that the user is indoors and the movement type indicator 35 gives an indication that the user is rather static. Indeed, together, especially during a day of work, those indications are very likely to reflect the user's sitting in front of a computer screen, or under an office's/home fluorescent/led light source.

In a second example, the behavioral index deriver 102 (e.g. module 22) derives the Blue Light Personal Exposure Index by calculating the percent of a most recent time period in which the indoors/outdoors indicator indicates that the user is indoors, and appears relatively static. In this regards the behavioral index deriver 102 may determine that the user appears static when either the accelerometer measured values are all below a reference value predefined by an administrator or programmer of system 1000, or the movement type indicator module 33 gives an indication that the user is static.

11) An average sun glare indicator module 23 is configured and operable to process the sensors data to determine an average/estimate of sun glare per the time frame/interval ATI. Each sun glare estimate may be calculated by the behavioral index deriver 102 (e.g. by module 23 thereof) by using a predefined method, say once in three minutes, for example, using the method illustrated in FIG. 5A-5B hereinbelow.

12) A day light indictor 24 is configured and operable to process the sensors data to determine wither during the respective the time frame/interval ATI is in daylight time. In one example, the behavioral index deriver 102 (e.g. module 24 thereof) determines the day-light indicator based on the user's location as measured by the position sensor 04 or based on location data obtained from location services by using location based Sunset/Sunrise times data, which are available to the general public over the internet (say on the AccuWeather.com® website) and which may be obtained by the data provider 100.2.

IV. Weather Indicators Module 40:

The weather indicators module 40 is configured and operable to carry out the methods described in the following in order to determine the weather conditions to which the user is exposed and may include for example the following sub-modules:

11) A temperature indicator 41 gives the average/nominal temperature in the user's geographical location(s), per a predefined time frame.

In one method/routine example, the behavioral index deriver 102 (e.g. the temperature indicator 41) determines/calculates the temperature indicator by averaging over values measured by a temperature sensor (not specifically shown) installed on the user's mobile device 1010 or wearable device during the respective time frame/interval ATI.

In a second method/routine example, there is rather used the location of the user as given by the values measured by the positioning/GPS sensor 04 or the location services 100.2—say using the user's location indicator 31, to retrieve the temperature. In the example, the temperature is retrieved from one of the databases available to the general public over the internet—say from the AccuWeather.com® website.

Thus, in one example, once in an hour, the behavioral index deriver uses the user's location and one of the publically available databases, say the AccuWeather.com® website, to determine the temperature for that hour. Then, say once a day, the behavioral index deriver calculates the average temperature indicator for the user's geographical location(s), by averaging over the determined temperatures.

12) A cloudiness indicator module 42 gives the percentage of cloudiness time during a predefined time frame/interval ATI. Namely it designates the percentage of sky coverage by clouds during the predefined time interval.

Optionally the behavioral index deriver 102 (e.g. module 42) determines/calculates the average cloudiness indicator based on location of the user as given by the values measured by the GPS receiver 04 or location services 100.2, and on one of the location based databases available to the general public over the internet—say from the AccuWeather.com® website.

Thus, in one example, once in a predetermined time period (e.g. once in every time interval ATI or once in an hour), the behavioral index deriver 102 (e.g. module 42) uses the user's location and the AccuWeather.com® website, to determine if the sky is cloudy in the user's geographical location. Then, the behavioral index deriver calculates the average cloudiness indicator by calculating the percentage of time of cloudy sky in the user's geographical location(s) during the time frame.

Thus in view of the above the behavioral index deriver is configured and operable to derive plurality of low level indicators pertaining to the lighting, environment and optionally the weather to which the user is exposed during one or more time intervals of the behavioral monitoring period, and also pertaining to the movement type of the user during these time intervals.

As indicated above the behavioral indexes may be derived by the behavioral index deriver 102 (e.g. by module 102.2 thereof) based on the values measured by the sensors 101 over a behavior monitoring time period BMP (say day of work or number of hours or few days or weeks). Typically the behavioral indexes are derived based on the above described lower level indicators, or on both the measured values and the lower level indicators.

Optionally, one or more of the behavioral indexes are updated every predefined number of time units (say hours)—say by the behavioral index deriver 102 of system 1000. Alternatively or additionally, one or more of the behavioral indexes are updated by the behavioral index deriver 102 when the behavioral index deriver identifies a predefined change in one of the measured values, or rather as a result of triggering by the user (e.g. via the UI) or by a remote server computer or by a service utility running on a remote computer, etc.

Each one of the behavioral indexes may be recalculated based on the lower level indicators 10, 20, 30 and/or 40 calculated during the predefined number of time intervals ATIs, or rather based on the lower level indicators calculated during a longer period which includes those predefined number of time intervals ATIs.

The behavioral indexes may include indices associated with at least two and sometimes three of the following behavioral indices categories: 50—Lighting indices; Activity type Indices 60, and general weather indices 70. As can be appreciated from the description herein above and below, lighting indices 50 may be used by the system (e.g. by module 103) to determine optical filters and/or coatings which should be implemented on the eyewear lenses. Activity type indices 60 are generally typically used by the system (e.g. by module 103) to determined preferable optical design of the lenses (the geometries and locations at which near-eyesight-vision, far-eyesight-vision and possibly also intermediate-distance-eyesight-vision should be located on the lens and the geometries (lengths/widths) and acceptable level optical aberrations of the transition region(s) (also known as corridor(s)) between them. Activity type indices 60 may also be used to determine eyewear frames and lens materials which suite the activities with which the user is engaged. The general weather indices 70 may also affect the preferred lens materials and/or the frame type or shape to be recommended to the user.

In general according to some embodiments of the present invention the behavioral index deriver (e.g. module 102.2 thereof is configured and operable to determine the behavioral indices by averaging or summing or accumulating the values of the lower level indicators which pertain to the respective indices over the time intervals ATIs of the of the behavioral monitoring period BMP during which the indicators are calculated.

In the following provided is a none limiting list of optional behavioral characteristics/indices which are derived for the user based on the behavior monitoring period BMP according to some embodiments of the present invention. The behavioral characteristics/indices may be determined by the behavioral index deriver 102 (e.g. by module 102.2 or sub-modules thereof), in conjunction with the optional sub modules 50-70 which may be included in the system an configured to derive them and in conjunction with one or more example routines/methods which may be executed by these respective modules to determine the values of each of these behavioral indices based on the low level indicators listed above and possibly also based the sensor data obtained by the value measurer 101. Thus the list of behavioral index derivation sub-modules may optionally include, but is not limited to any one or more of the following:

I. Lighting Indices/Characteristics Module 50:

The Lighting indices/characteristics module 50 may be configured and operable to carry out one or more of the following methods and/or include one or more of the following personal index deriver modules to determine the personal characteristics/indices of the lighting conditions to which the user is exposed during the behavioral monitoring period:

1) A UV personal index deriver module 51 is configured and operable to determine a personalized value of the UV radiation to which the user is exposed during the behavioral monitoring period BMP.

Optionally, UV personal index deriver module 51 is configured and operable to derive the UV personal index by processing (e.g. accumulating or averaging) the values of one or more of the lower level indicators such as the UV light indicator 21 described hereinabove.

In another example, the UV personal index is derived using a function based on the values of user's UV indicator, indoors/outdoors indicator, cloudiness indicator, current time, sun elevation, etc. or any combination thereof, which are determined per each of the plurality of time intervals ATIs during the behavioral monitoring period as described in further detail hereinbelow.

For instance, the function may be based on a percentage of the recent three hours spent by the user outdoors.

To this end, the indoors/outdoors indicator may be calculated per a predefined time frame/interval, and accordingly, the UV personal index is derived on basis of the indoors/outdoors (environmental indicators 10 which correspond to the time interval, respectively. The percentage of the time intervals ATI spent by the user outdoors is calculated by adding to the number of time intervals ATI for which the indoors/outdoors indicator indicates a time spent by the user outdoors, half the number of times intervals for which the indoors/outdoors indicator indicates a time spent by the user partially indoors and partially outdoors, dividing their sum by the number of time intervals, and multiplying by one hundred. In the example, the function may give the UV personal index, by multiplying the percentage of the time intervals spent by the user outdoors by the average UV indicator for these respective time intervals and the average cloudiness indicator at these time intervals.

2) A sun glare personal index deriver module 53 is configured and operable to determine a personalized value of the average sun glare indicator 23 to which the user is exposed during the behavioral monitoring period BMP.

Optionally the average sun glare personal index 53, is determined through a function of the user's location indicator 31, his movement direction indicator 34, percentage of the user's time which the user spends outdoors (indicator 12), the time (e.g. the sun's position in the sky as determined by the date/time information) and/or the weather conditions indicators 40 (e.g. cloudiness indicator 42) and/or any combination thereof, as measured during the plurality of the time intervals ATIs of the behavioral monitoring period.

In the one example, the sun glare personal index deriver module 53 determines the sun glare personal index by a multiplication function of the percentage of time intervals ATIs spent by the user outdoors (indicator 12) multiplied by the sun glare indicator 23 and averaged over the time intervals ATIs.

In another example, the function is further based on the average cloudiness indicator 42 for the respective time intervals (namely the average of the sun-glare indicator value 23 multiplied by the percentage of time the user spent outdoors (indicator 12) and further multiplied by the cloudiness indicator 42) averaged for the rime intervals ATIs of the behavioral monitoring period BMP.

3) A blue light index deriver module 52 is configured and operable to determine a personalized estimate on the user's exposure to High Energy Visible Light (HEV).

Optionally according to one method the blue light index deriver module 52 is configured and operable to determine the average blue light index deriver module 52, based on a function of the average of the blue light indicator 22 as measured during the plurality of the time intervals ATIs of the behavioral monitoring period BMP.

Yet additionally or alternatively, according to some embodiments of the present invention the system utilizes the activity type indicators to determine the blue light exposure of the user. For instance, in some embodiments the reference data RDB includes blue/HEV light reference data associating/assigning different values/grades/levels of blue/HEV light exposure to different activities of the user. As an example: Office environment is assigned with 25% grade/level of blue light exposure; watching TV is assigned with 50% grade; sitting in front of a computer is assigned with 100% grade. Then based on the activity type/indicator of the user and/or based on the location/environment indicators determined for the user for various time intervals ATI (e.g. home/office/in-doors/outdoors) the blue light index can be determined. This may be based on a proper mathematical function, such as weighted averaging of the blue light grades indicated in the reference data while weighting them with the percentage of time (namely weighted by the time intervals) the user spends in each environment.

II. Activity Type Indices/Characteristics Module 60

The activity type indices/characteristics module 50 may be configured and operable to carry out one or more of the following methods and/or include one or more of the following personal index deriver modules to determine the personal characteristics/indices of the lighting conditions to which the user is exposed during the behavioral monitoring period:

4) A transition frequency index deriver module 61 is configured and operable to determine the frequency in which the user switches from outdoor light conditions to indoor (say office) light conditions.

Optionally, the transition frequency index deriver module 61 is configured to determine the transition frequency personal index from one or more of the lower level indicators calculated from the values measured by the sensors—say from the environmental indicator 10, location switching indictor 11, average cloudiness indicator 42, average sun glare indictor 23, etc., or any combination thereof.

In a first example, the transition frequency personal index is determined for the behavioral monitoring period BMP by summing or averaging the values of the location switching indictor 13 over the behavioral monitoring period BMP.

In a another example, the transition frequency personal index 61 is derived from the location switching indictor, average cloudiness indicator, and average sun glare indictor, say by multiplying the averages of those three indicators during the behavioral monitoring period BMP.

5) The activity types home, office driving, and sport characteristics of the user and their durations may be determined by one or more modules/method 62 to 65 which are referred to herein as: home personal index deriver 62, office personal index deriver 63, driving personal index deriver 64, and sports personal index deriver 65, which may be included in the system. These modules/methods 62-65 and possibly also additional/other methods/module pertaining to other or more specific activity types may be included/employed by system 1000 to determine the level (or the percentage of time) the user invests in each type of activity which might impose different eye/visual requirements/behavior from the user. These modules/methods 62-65 and/or possibly additional/other modules pertaining to different activities are configured to determine the duration and type for each consecutive activity of the user. This may be based on the value of the movement type indicator 33 measured during the time intervals ATIs of the behavioral monitoring period BMP, for example by counting the number of time intervals ATIs or equivalently the total time or percentage of time during the behavioral monitoring period BMP at which the user is engaged with each activity.

Thus, in one example, the behavioral index deriver (e.g. modules 62-65 thereof) identifies consecutive time periods made of time frames/intervals for which the movement type indicator is calculated (as described in further detail hereinabove), and for which the calculated movement type indicator indicates a same movement type.

For instance, the movement type indicator is calculated per each time frame of ten minutes, and the behavioral index deriver identifies three consecutive ten minutes long time frames for which the movement type indicator indicates a running of the user.

In the example, the activity types and duration index may be derived as a matrix in which each line has two entries, one holding a movement type and another holding a consecutive time period which is the movement's duration. Consequently, a first one of the lines holds a 'user running' indication in one entry and a '30 Min.' indication in a second entry.

In the example, the behavioral index deriver further identifies two consecutive ten minutes long time frames for which the movement type indicator indicates a sitting of the user. Consequently, a second one of the lines holds a 'user sitting' indication in one entry and a '20 Min.' indication in a second entry.

In a particular example the A driving time personal index module 64 is configured and operable to determine an estimate on the user's driving time, say on basis of the movement indicators 30, and/or the duration of user's time spent indoors as estimated based on the indoors/outdoors indicators 10, the speed indicator 35, etc., or any combination thereof.

Thus, in one example, the driving time personal index module 64 derives the driving time personal index, by counting the number of time intervals during the behavioral monitoring period in which the speed indicator 35 indicates that the user moves in a speed characteristic of driving rather than of cycling, walking or running—say when the user's speed is higher than 25-40 Kilometers/Hour.

III. Weather Indices/Characteristic Deriver Module 70

According to some embodiments of the present invention the system further includes a weather indices deriver module 70 which may be configured and operable for determine certain indices such as the average temperature index 71 and the temperature change personal index 72 which respectively give an estimate on average environmental temperature and the average temperature changes experienced by the user, on frequency of such changes, or on both. According to some embodiments the weather indices deriver module 70 according to the user's location switching indictor 13, indoors/outdoors indicator 11, temperature indicator 41, or any combination thereof.

Thus, in one example, the behavioral index deriver derives the Temperature Change Personal Indices 71 and 72 under an assumption that the indoors temperature at predetermined environments is kept at predetermined values (e.g. in "office environment" the in-doors temperature is typically kept at 22° C. while at home environment it may be kept at 25° C.). This may be based on reference data sorted in the RDB and associating various predetermined in-door environments/locations with various respective temperature conditions.

Optionally, in the example, each time the indoors/outdoors indicator switches from an indication that the user is indoors to an indication that the user is outdoors, the behavioral index deriver calculates the difference between the average temperature indicator outdoors and the predetermined reference temperature (e.g. 22° C.) of indoor locations. Alternatively or additionally the system may utilize the activity indicators to determine whether the user is driving (in-vehicle) or he is switching in\out of a vehicle, and determine the difference between the average temperature indicator outdoors (e.g. a sunny\cold day) and the reference temperatures kept at sunny/cold days.

Optionally, in the example, the temperature change personal index is derived by the behavioral index deriver per each pre-defined period of time ATI (say every ten hours), in which case, the behavioral index deriver derives the temperature change personal index by summing up the differences calculated for that per-defined time.

Alternatively, in the example, the behavioral index deriver derives the temperature change personal index by summing up the difference calculated for that per-defined period of time and dividing the result of the summing, by the sum of location switching indictors for that per-defined time period, to yield the temperature change personal index.

Turning now to FIG. 3B, in the method/system of the present invention, the eyewear specification is generated 330 based on passive learning of the user's needs from the user's behavior through a time period of the measuring of the values, say through one or more of the user's day of work or through a number of hours, as described in further detail hereinabove.

Optionally, the eyewear specification is generated 330 by the Eyewear Specification Generator module 103 from one or more of the above described behavioral indexes (e.g. the lighting indices 50, the activity type indices 60, and possibly also the weather indices 70) as described in further detail hereinbelow. Additionally or alternatively, the generation 330 of the eyewear specification may be further based on one or more of the calculated lower level parameters.

For example, the generation 330 may be additionally based on the user's average temperature indicator, percent indoors indictor, indoors/outdoors indicator, a time spent by the user at specific locations—say at a Golf Club, Gymnasium, etc. as calculated using the location indicator, etc., or any combination thereof.

Optionally, the generated 330 specification includes one or more eyewear features—say a feature of lenses or of a coating to be applied to the lenses in the eyewear's manufacturing process. For instance as shown in FIG. 3B, the eyewear features of the generated 330 specification may include but are not limited to: (I) Lenses coatings and/or filters such as: E-SPF (Eye-Sun Protection Factor), Anti-Glare Coating, Anti-Reflection Coating, Photochromic Lens Types, Blue Light (HEV) Protection Coating, Anti-Fog Coating; (II) optical lens designs such as Progressive Addition Lenses (PAL) designs suitable for specific/special purposes such as Driving, Golf, or Office Use, and/or customary designed for the user based on his behavioral characteristic; and/or (III) frame types and/or lens materials selected as per the users characteristic behavior.

Optionally, the generation 330 of the specification provision of reference data (e.g. stored in a data-storage RDB) including reference values for one or more of the behavioral indexes in association with and with respective eyewear features suitable for use by users for which their behavioral indices are similar to the respective reference values. The reference value may be predefined, say by an administrator or programmer of system 1000 or rather automatically (say by the eyewear specification generator). The features of the eyewear specification may be determined by comparing the above determined indices 50, 60 and/or 70 to their respective reference values.

Thus, Eyewear Specification Generator module 103 may include one or more of the following methods/modules 80, 90, 95 and 97 or their sub-modules/methods as described in more details below, which are configured and operable together for generating the eyewear specification. These may include but not limited to one or more of the following:

I. Filters and Coatings Specification Generator 80

As indicated above the Filters and Coatings specification generator 80 may be adapted to determine eyewear specification features m including data indicative of one or more coating or filters of a specific lens color, or a specific filter for the lenses to have, on basis of the user's sun glare personal index, or location indicators (For example, upon the location indicators indicating that the user spends a few hours a day on a beach). Similarly, the generated 330 specification may additionally or alternatively include an anti-scratch coating upon the user's activity type and duration index indicating that the user spends his time playing Basketball or Tennis, etc.

More specifically the Filters and Coatings specification generator 80 may include the following modules methods adapted to determine respective coatings to be included in the eyewear specification of the user:

1) E-SPF (Eye-Sun Protection Factor) coating module 81.

E-SPF is an internationally recognized rating standard which indicates the UV protection provided by a lens. The higher the E-SPF value, the more protection the lens provides the user with. For example, lenses with an E-SPF value of 15 provide a level of protection which is 15 times higher than when without any UV protection.

Optionally, the eyewear specification generator 103 of system 1000 or the eyewear specification generator 103 assigns a thus predefined reference value to the UV Personal Index 51. For example, the eyewear specification generator 103 may calculate the reference value using an average UV Exposure for the geographical region in which the user spends his time in (say San-Francisco) and an average number of clear sky (no clouds) in the geographical region—both taken from one of the databases publically accessible over the internet (say from the AccuWeather. com® website).

Thus in one example, a publically accessible weather database indicates for the recent three months in the San-Francisco area, an average UV Exposure of 9.0, and a clear sky for 80% of the days of those three months. Consequently, the eyewear specification generator sets the reference value for the UV personal index at 7.2 (9.0×80%).

In the example, the eyewear specification generator compares the UV personal index 51 derived for the user (say by the behavioral index deriver), to the reference value of 7.2, say by calculating the difference between the UV personal index derived for the user and the reference value of 7.2 (say by subtracting the two).

Then, the eyewear specification generator uses the calculated difference, for determining the Eye-Sun Protection Factor (E-SPF) to be included in the specification.

Optionally, the eyewear specification generator 103 further uses a reference database RDB (e.g. table) which may include predefined reference values for determining the E-SPF. The table may include reference data associating a recommended E-SPF coating value per each range of UV personal index.

Optionally the reference data may be e periodically updated by the eyewear specification generator 103 according to a statistical model run over differences between a UV personal index and the reference value as previously calculated for users in the San-Francisco area, say using standard Normal Distribution Statistics, as known in the art.

Thus, in one example, the predefined table includes ten lines. Each line pertains to one of ten deciles of the users and gives the difference range and the recommended E-SPF value for that difference range between a UV personal index and the reference value.

Thus, in the example, the eyewear specification generator may generate a specification which includes an E-SPF of 15 for a first user, and a one of 25 for a second user, on basis of a comparison of their respective UV personal indexes with the reference data. The reference value represents a combination of the average UV Exposure and the percentage of clear sky days in a certain location (e.g. San-Francisco), where both users reside.

2) An Anti-Glare Coating module 82.

Anti-Glare Coating may include for example, a coating which serves to protect the eyes from sun glare.

Accordingly, optionally, the eyewear specification generator 103 of apparatus 1000 assigns a thus predefined reference value to the average sun glare index.

Optionally, the eyewear specification generator 103 sets the reference value for the average sun glare index to a maximal value, say to 1 or 100%, as per the range of values which the average sun glare Index may have.

Alternatively, the eyewear specification generator obtains the reference value for the average sun glare index a reference database/storage RDB (on basis of data provided an expert physician).

In one example, the eyewear specification generator 103 (e.g. module 82 thereof) compares the average sun glare index 53 derived for the user say by the behavioral index deriver 102, to the reference value(s) to determine a match between them, (e.g. say by calculating the difference between the average sun glare index derived for the user and the reference value(s) (say by subtracting the two)).

Then, the eyewear specification generator uses determined match (e.g. the calculated difference), for determining the anti-glare coating to be included in the specification.

Further in the example, the eyewear specification generator may utilize reference data (e.g. a table which may be predefined and stored in the reference database RDB), for determining the anti-glare coating. The reference data may include a recommended level of anti-glare coating or sun glasses chromatic/polarizer filter/color per each range of values of the average sun glare index 53 of the user.

Optionally the reference values are periodically updated by the eyewear specification generator according to a statistical model run over the differences as calculated for users of apparatus 1000 in a recent predefined time, say in recent one month.

Thus, in one example, the predefined table include ten lines, and each line in pertains to one of the ten deciles of the users and gives the difference range and the recommended anti-glare coating level, for that decile.

Thus, in the example, the eyewear specification generator 103 may generate a specification which includes one anti-glare coating level for a first user, and a higher one to a second user, on basis of a comparison of each user's average sun glare indexes with the reference value.

3) Photochromic filters module 83

Photo-chromic lenses include lenses of different types. The Photo-chromic lenses dynamically change their color—say by darkening automatically when exposed to sunlight, and fading back when indoors.

Optionally, the eyewear specification generator 103 includes Photochromic filters module 83 which assigns a thus predefined reference value indicative of the type of Photochromic lens/coating to be used based on the transition frequency personal index 61 determined for the user.

Optimally, the eyewear specification generator obtains reference data associating Photochromic filters with various ranges of the user's transition frequency personal index 61 from a reference database/storage RDB (on basis of data provided an expert physician).

Alternatively or additionally, optionally, the eyewear specification generator 130 calculates and assigns the reference value by averaging over all transition frequency personal indexes of plurality of users of the system 1000 (in case the system is at least partially implemented in a server computer 1002) which may be derived per user, within a predefined hours range (say from 9 AM to 5 PM), in days of clear sky (as indicated say by the AccuWeather.com® website), in recent month. Then, on a clear sky day, if the user's frequency personal index 61 as derived per hour, from 9 AM to 5 PM, is significantly higher than that reference value, say more than 80% higher, the eyewear specification generator may generate a specification which includes Photochromic lenses of a type optimized for general use on a sunny day.

4) Blue Light (HEV) Protection Coating module 84.

High-energy visible (HEV) radiation or blue light, though having longer wavelengths and lower energy than UV light, can penetrate deeply into the eyes and cause retinal damage, as described in further detail hereinabove.

Optionally, the eyewear specification generator 103 (module 84 thereof) is configured and operable to determines if the user needs a Blue Light (HEV) Protection Layer, the type of the HEV protection layer needed, or both.

For determining if the user needs a Blue Light (HEV) protection layer or the type of HEV protection layer needed, the eyewear specification generator may use the user's blue light personal exposure index 52, activity type and duration indices 60, indoors/outdoors indicator 10, etc., or any combination thereof.

Optionally, the eyewear specification generator obtains reference data associating various blue light coatings/filters with reference values of the user's blue light personal exposure index 52 from a reference database/storage RDB (on basis of data provided an expert physician).

Alternatively or additionally the eyewear specification generator calculates an average of blue light personal exposure indexes previously derived for multiple users of 1000 thorough time periods in which their indoors/outdoors indicators indicate that the users are indoors.

Then, by matching the reference value(s) of blue light personal exposure in the reference data to the blue light personal exposure index 52 of the user or by calculates a difference between a certain reference value of the blue light personal exposure index and the blue light personal exposure index 52 derived for the user the Blue Light (HEV) Protection Coating module 84 determined a value for the HEV protection coating suitable for the user.

Further in another the example, the eyewear specification generator uses a table or reference data RDB which may be predefined, say by the administrator or programmer of system 1000, for determining a value for the HEV protection coating. The table gives a recommended level of HEV Protection coating per each range of blue light personal exposure index 52 of the user. Optionally the reference data is periodically updated by the eyewear specification generator according to a statistical model run over the differences as calculated for users of system 1000.

Thus, in one example, the predefined table includes ten lines, and each line in the table pertains to one of the ten deciles of the users, and gives the difference range and the recommended HEV protection coating level, for that decile.

Thus, in the example, the eyewear specification generator may generate a specification which includes one HEV protection coating level for a first user, a higher one to a second user, an no HEV protection coating for a third user.

The specification generated 330 (say by the eyewear specification generator) may include, for example, an HEV protection layer of a specific type—say a coating of a slightly yellowish color of a specific material, as known in the art.

5) Anti-Fog Coating module 85.

Anti-Fog coating may be relevant, for example for a user who experiences frequent temperature changes or for a user who spends time in cold temperatures—say for a user who jogs frequently in winter mornings. Both the temperature changes and the cold temperatures are likely to result in the user's fogging his glasses.

Optionally, the eyewear specification generator 103 includes an Anti-Fog Coating module 85 which is configured and operable for chooses/selects an anti-fog coating for the eyewear specification, on basis of the user's temperature change personal index 72, average temperature index 71, or both.

Thus in a first example, the eyewear specification generator (e.g. module 85 thereof) generates a specification which includes an anti-fog coating when the temperature change personal index 73 exceeds a predefined threshold which may be stored in the reference database RDB.

The threshold (i.e. a reference value) may be predefined by an administrator of system 1000, or rather be calculated by the eyewear specification generator on basis of temperature change personal indexes derived for other users of system 1000, say in recent month. Optionally, for calculating the threshold, the eyewear specification generator 103 uses standard Normal Distribution Statistics, as known in the art. Alternatively, the eyewear specification generator may calculate the threshold, on basis of say the fifty highest temperature change personal indexes derived for the other users of the system 1000.

Optionally, the other users are users of system 1000 selected by the eyewear specification generator according to their presence in a same cold country or region as the user, on their having a same profession as the user's, etc.

In a second example, the eyewear specification generator generates a specification which includes an anti-fog coating when the user spends more than two hours daily outdoors (as per the user's indoor/outdoor indicators 10) in hours in which the temperature outside is lower than a predefined threshold—say below 7° C.

II. Optical Lens Design Module 90

As indicated above the optical lens design module 90 module/specification-generator 90 may be adapted to determine eyewear specification features including data indicative of one or more optical features of the lenses.

Typically the optical lens design module is adapted to determine the design of optical lenses, such as but not limited to PAL lenses, by utilizing reference data associating each user activity with a certain reference values of one or more viewing characteristics of the user during the respective activities. For instance, each user activity (e.g. office/computer related activities and/or various types of sport activities and/or various types of home activities and/or driving activities) may be generally characterized by certain nominal values of reference parameters as:

- Nominal eye focusing distance (viewing distance):—indicating the nominal distance to which the user's eyes are normally focused during the activity;
- Gaze direction (e.g. gaze pitch orientation and/or yaw namely being the a vertical/horizontal gaze angles):—indicating nominal direction/pitch angle of the user's gaze during the activity (and gaze direction will normally include a vertical/horizontal gaze angle;
- Viewing angle:—indicating the angular range of the gaze's yaw and possibly pitch orientation(s) during the activity (e.g. this is also typically known as a field angle).

Figure 6D:
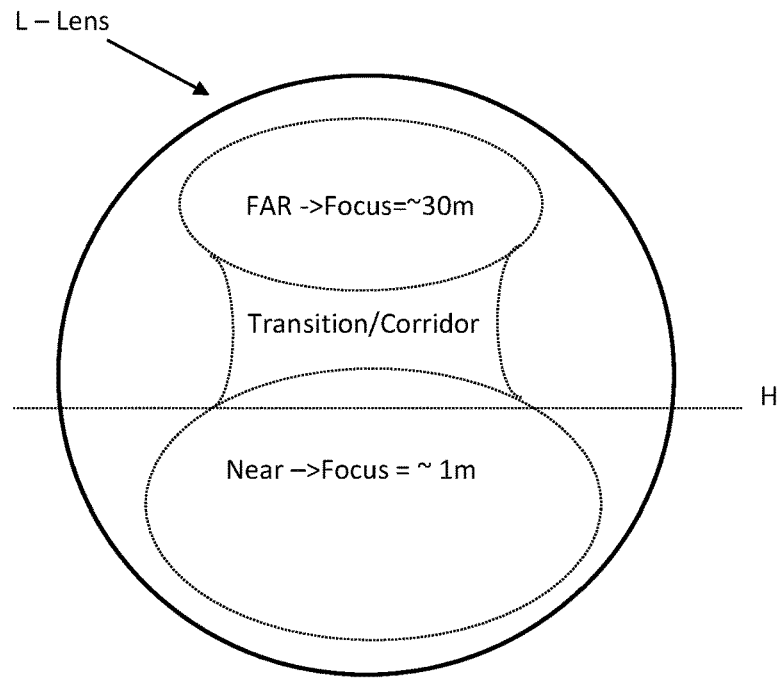

FIG. 6A shows a table exemplifying in self explanatory manner certain nominal reference values of the above described viewing parameters as per the as per several activity types. Reference data including data such as that illustrated in the table of FIG. 6A for a plurality of activities (e.g. and/or lens usage parameters, such as the gaze orientations associated with the respective activities), may be stored in a reference database RDB and used by the Optical Lens design module 90 to determine the optical parameters of the lens design based on the behavioral indexes and particularly the activity type indices 60 determined for the user.

6) A custom PAL design module 94

According to some embodiments of the present invention the Optical Lens design module 90 includes a custom PAL design module 94 which is configured and operable for generating custom PAL lens design suitable for the user based on the activity type indices 60 determined for the user.

According to one example, the custom PAL design module is configured an operable to generate a focusing distance spatial lens map indicative of the average nominal distances to which the user eyes are focused when looking through each region of the lens. This may be performed by utilizing the reference data of viewing parameters as illustrated in FIG. 6A above together with the activity index data 60 as described above an also illustrated for example in a table in FIG. 6B.

For instance the spatial lens map may be may be generated by the Optical Lens design module 90 by carrying out the following for example:

(i) Taking an average of the nominal focusing distance parameter of each activity (as specified for example in FIG. 6A) multiplied by the duration of this activity by the user (e.g. the daily percentage of the activity duration from the user's day as specified for example in FIG. 6A) and integrating it over the viewing region of the lens which is used by the user during each activity. In this regards the viewing region of the lens as may be defined by the Lens region usage parameters of the reference data of FIG. 6A, namely the Nominal gaze direction and the nominal viewing angle of users during each of the activities. This provides a spatial focusing map M of the lens as shown for example in FIG. 6C indicative focusing distances to which the user focuses his gaze when looking through various regions of the lens;

(ii) Then spatial focusing map M of the lens may be segmented into near eyesight vision area, far eyesight vision areas and possibly additional focusing areas (e.g. intermediate focusing area in accordance with the locations of region having similar/like focusing distances (possibly/typically similarity may be determined in logarithmic scale or other suitable) and the corridors/transition regions between them. This results with a spatial map L of custom PAL lens design such as that illustrated in FIG. 6D.

Thus the custom PAL design module 94 may be configured and operable in accordance with the method described above or with any other suitable method in order to determine a custom optical PAL lens design based on the user's behavioral indices determined by the behavioral index deriver 102. The PAL lens design may include data indicative of the geometries and locations at which near-eyesight-vision, far-eyesight-vision and possibly also intermediate-distance-eyesight-vision should be located on the lens (these parameters are also commonly known as the (Far Measuring Position, Near Measuring Position and Corridor of the lens), and also the geometries (lengths/widths) of the near-eyesight-vision, far-eyesight-vision and possibly also intermediate-distance-eyesight-vision zones in the lens (parameters generally known as the Far Zone, Near zone and possibly also Intermediate Zone and their width/heights). Additionally the system may be configured and operable to determine in this way the location and geometry of the Corridor(s) zone(s) between the above zones (e.g. distortion free path e.g. eye-path or convergence path) and acceptable level optical aberrations of the transition region(s) (also known as corridor(s)) between them.

More specifically the technique of the present invention allows to determine the above and optionally additionally or alternatively the following features of the PAL lens:

Far Measuring Position: The position at which if measured using a lens-meter, the prescribed far power is verified. This position is marked on the centration chart, above the Fitting point.

Near Measuring Position: The position at which if measured using a lens-meter, the prescribed near power is verified. This position is marked on the centration chart, below the Fitting point.

Far Zone: A region within a lens intended to be used for viewing objects a distance over 6 meters, in which the mean power does not deviate from the prescribed far power by more than about 0.5 Diopters (denoted by [D]).

Far Zone Width: length of a horizontal line through the Fitting Point, where residual cylinder <0.5 D, 0.25 D Near Zone: A region within a lens intended to be used for viewing objects a distance closer than 60 centimeters, in which the mean power does not deviate from the prescribed near power by more than about 0.25 [D].

Near Zone Width: length of a horizontal line through the Near Measuring Position, where residual cylinder<0.5 D, 0.25 D, and the Add>MaxAdd−0.25[D].

Corridor: A region within a lens stretching between two zones, the Far Zone and Near Zone along a convergence path on which the measured mean power continuously increases, where the mean power is not less than the Prescribed Far power, and not greater than the Prescribed Far power+The Prescribed Addition+0.1, 0.25, or 0.5 [D], and the unwanted astigmatism is <=0.12, 0.25 or 0.5 [D].

Corridor Length: the distance between the lowest point in the far segment (below cylinder threshold), highest point in near segment (above Min Add threshold, below Max cyl' threshold, or below max add power).

Intermediate/Transition Zone: The transition zone is defined along the convergence path from the vertically lowest point below the fitting point, where the addition is still zero to a point along the convergence path in the near vision zone where a full addition is reached. The short transition zone allows a smooth transition, with less distortion, from the far to the near zones and vice versa with a continuous and monotonic power rise, without any: power jump, prism jump, or image jump.

Convergence Path: is a line made of points on the back surface of the lens through which the eye must gaze in order to view an object located horizontally between the two eyes at the defined distance for each given elevation in focus, accounting for the refractive power of the lens.

Viewing Angle:

More specifically the Lens Design Parameters may include the following:
 Corridor (Width/shape; Location; Length)
 Near Zone (Size/Width; Position; Inset; Shape)
 Far Zone (Size/Width; Position; Shape)
 Other custom Zones (Size/Width; Position; Shape)
 Peripheral Aberrations (maximal aberration and/or its position; maximal aberration's gradient and/or its position)

The above described feature of the PAL lens design may be determined relative to the so called Fitting Point of the lens, which is the position on the lens through which a patient gazes when looking straight ahead at an infinite (or equivalent) distance. The Fitting Point position may also be used according to the present invention in order to determine a fit/cut contour of the lens within the selected frame according to the user requirements/need. When depicting a PALs with a contour plot, the geometric center of the lens is often located at the (0,0) position. However, the fitting point is commonly designed located at the geometric center or 4 mm above, e.g. (0,4).

In some embodiments the custom PAL design module 94 is further configured and operable to utilize the behavioral indices (particularly the activity type indices 60) to determine whether the user uses any particular region of the lens for viewing significantly different focusing distances (e.g. the difference between the focusing distances may be measured/normalized of example in logarithmic scale). In this case the custom PAL design module 94 may determine that a single eyewear may not provide good enough solution for the user or that general PAL lens designs suitable for the plurality of the user activities are conflicting. In this case the system may operate in at least one of the following manners: Utilize a combining strategy to generate a combined lens design based on the predetermined/monitored combined activities of the user. For example combining strategy may include weighting the user activities based on their activity types, durations, and similarity between them and in the case where two activities or similar groups or activities have conflicting optical requirements, the system chooses the higher weighted activity (and possibly recommends a preference of two or more sets of eyewear). To this end the system may issue a corresponding notification to the user (e.g. via the UI module).

Figure 6E:
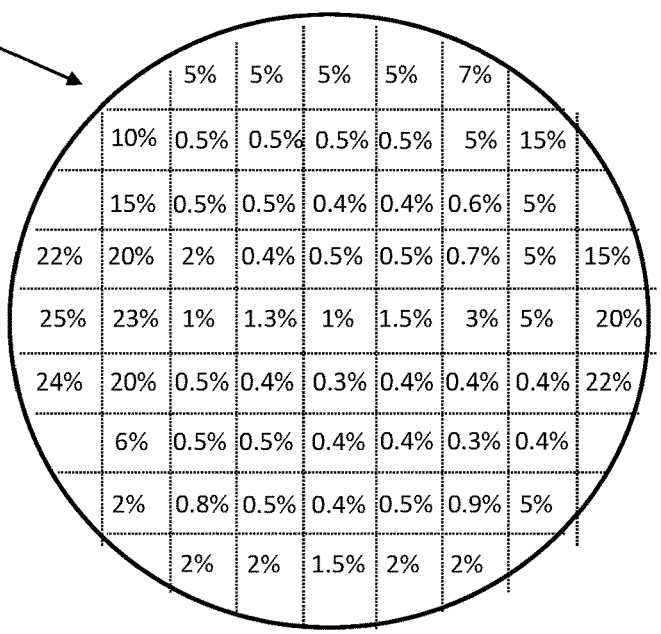

For instance in some embodiments the custom PAL design module 94 processes the reference data of viewing parameters as illustrated in FIG. 6A above together with the activity index data 60 as described above an illustrated for example in a table in FIG. 6B to determine a standard deviation map S indicative of the standard deviation of the focusing distances to which the user eyes are focused when looking through each region of the lens throughout the plurality of activity types in which the user is engaged. For instance, a standard deviation map S such as that illustrated in FIG. 6E may be generated by the Optical Lens design module 90 by carrying out the following for example:

(i) Taking a standard deviation of the nominal focusing distance parameter of each activity (as specified for example in FIG. 6A) multiplied by the duration of this activity by the user (e.g. the daily percentage of the activity duration from the user's day as specified for example in FIG. 6A) and integrating it over the viewing region of the lens which is used by the user during each activity. This provides a spatial standard deviation map S of the focusing distances required from the lens at each region thereof as shown for example in FIG. 6E;

(ii) Identifying areas/regions in the lens at which the focusing standard deviation exceed a certain predetermined focusing standard deviation threshold (e.g. in logarithmic or other scale);

(iii) In case areas/regions of large standard deviation, larger than the threshold are identified, the custom PAL design module 94 determines that a separate/distinct eyewear may be required for these regions/areas and/or for the particular user activity causing the large standard deviation. In this case the custom PAL design module 94 may further process the activity indices and the reference data (e.g. such as those illustrated in FIGS. 6A and 6B) to determine the particular user activity(ies) causing the large standard deviation;

(iv) Then the custom PAL design module 94 may recommend on specific eyewear to suite this particular activity(ies).

To this end, in some cases specific eyewear having specific optical lens designs suitable for certain particular activities of the user may be recommended to the user based on his activity indices 60. This may for example include driving eyewear having driving PAL lens design; sports eyewear having sports PAL lens design office eyewear having office PAL lens design or other such as eyewear with custom PAL lest design suitable for one or more and possibly all the user activities with which the user is engaged.

For instance the Optical Lens design module 90 may include specific PAL design modules such as the driving PAL design module 92 Office Pal design module 91, sports PAL design module 93 and/or other specific pal design modules which may be configured and operable to process the activity indices 60 of the user and determine whether the user is particularly engaged with one or more activities (e.g. driving, office, sport activities) and in this case determine suitable PAL lenses for the user that match the respective particular activities with which he is engaged.

In this connection the system may include a PAL design reference data including certain specific PAL designs suitable for driving, office activities, various sport activities and/or other activities such as:

various specific driving activities (outdoors): Driving in urban/Country roads or off road, Day\night driving, Driving irregularly with frequent stops and accelerations,
 various specific Cycling activities (outdoors): On Road Cycling\Off road Cycling;

various specific water sport activities: Sailing/surfing; other sports such as Ski, Golf, Gym, Running;

Various specific office activities: Reading, Computer/Mobile Device use, Meetings;

Other/home activities Cooking such as Playing, Computer, Reading, Television/Gaming, Gardening (outdoor),Cleaning/housework.

The reference database may include reference PAL designs specific to several of the above listed activities or their combinations. Alternatively or additionally, reference PAL designs may include the following Lens Design Classes (activity optimized):All Purpose (Classic); Fashion (wrap lenses); Sport (wrap lenses); Golf; Urban; Office/Office E; Relax; Driving.

In the following, for clarity, only a few prominent PAL design modules are described including the Driving PAL design module 92; the Sports Pal design module 93 and the Office PAL design module 94. All these specific modules may be associated with the reference database RDB including reference PAL designs for specific activities and may be configured and operable for selecting specific PAL designs suitable for the activities with which the user is engaged in accordance with his behavioral indices.

7) Driving PAL design module 92 Features.

According to some embodiments of the present invention the Optical Lens design module 90 includes a driving PAL design module 91 which is configured and operable for determining PAL lens design suitable for the user based on the driving activity 60 of the user.

As indicated above for driving PAL, the important behavioral indices which are considered are those indicative of the duration, location, and time (e.g. lighting conditions) of the driving. The driving duration is used for weighting the overall recommendation, or a threshold for recommending drive eyewear. The driving location may be used for determining design parameters, (e.g. urban viewing environment objects will be closer than rural). Time of day during which the user typically drives may be used to determine an interference coating-manage sun glare, or artificial light source glare, or enhance contrast with a yellow filter.

A user who spends a significant part of his time driving, may need his eyewear to includes features which make the eyewear better suit driving—say certain types of frames or lenses, etc., as described in further detail hereinbelow.

Optionally, the eyewear specification generator 103 (module 92) of system 1000 determines that the user needs to have one or more features which better suit driving, and chooses one or more of those features for the specification, on basis of the user's activity type and duration index, driving time personal Index, etc., or any combination thereof.

In one example the eyewear specification generator (module 92) sets a reference value which reflects the number of driving hours, say on basis of statistical data or official standards available from government agencies such as the US Department of Labor or the US Department of Transportation, say to nine hours.

In the example, the eyewear specification generator compares (module 92) the user's daily number of driving hours as taken from the activity type and duration index entries which relate to driving, the driving time personal index 64, or both (say by calculating the average of the two), to a predetermined reference value (say the nine hours).

Further in the example, the module 92 of the eyewear specification generator 103 may use a reference table/database RDB which may be predefined, say by the administrator or programmer of system 1000, for determining if the user needs any one or of the features which make the eyewear better suit driving, and the features needed.

Optionally, the table gives a recommendation on the features needed per each range of differences between the user's daily number of driving hours and the reference value.

Thus, in one example, the predefined reference data table include ten lines, and each line in pertains to one of the ten deciles of the users, and gives the difference range and the recommended features (if any) for that decile.

Thus, in the example, the eyewear specification generator may generate a specification which includes features such as a polarization coating level or a specific Progressive Addition Lenses (PAL) type suitable for professional drivers—for a first user, and a specification which lacks those features—for a second user.

8) Office PAL (Progressive Addition Lenses) design module 91

According to some embodiments of the present invention the Optical Lens design module 90 includes an office PAL design module 91 which is configured and operable for determining PAL lens design suitable for the user based on the office activities 60 of the user, e.g. and/or any subset of office activities with which the user is primarily engaged.

One of the fastest growing PAL categories are lenses specifically designed for computer use and office environment, also known as Office PAL or Computer PAL.

These lenses place a computer viewing area of the lens straight ahead so that the user need not tilt his head back to find a clear spot to see his computer screen.

Progressive Addition Lenses (PAL) with such features ergonomically correct posture, reduce/prevent neck and shoulder tension, and computer vision syndrome, which are very typical when working in an office.

Optionally, the eyewear specification generator 103 (module 91 thereof) of system 1000 chooses Office PAL for the specification, on basis of the user's activity type and duration index, percent indoors indictor, etc., or any combination thereof.

Thus, in a first example, the module 91 generates a specification which includes Office PAL on basis of the activity type and duration index—say when the activity type and duration index indicated that the user spends many hours a day sitting.

Optionally, in the example, the eyewear specification generator (module 91 thereof) further uses additional parameters for determining whether to include Office PAL in the generated 330 specification, say a percentage of time in which the user spends outdoors as calculated from the user's indoors/outdoors Indicators or percent indoors indictor.

Thus, in the example, the eyewear specification generator (module 91 thereof) calculates the average daily number of hours spent by the user indoors, from the indoors/outdoors indicators of the user as derived in a recent period of say, one week.

In the example, the eyewear specification generator compares that averaged daily number of hours spent by the user indoors to a reference value, say to nine hours which is a typical number of workday hours in many countries.

Further in the example, the eyewear specification generator uses a reference data/table RDB which may be predefined, say by the administrator or programmer of system 1000, for determining whether to include Office PAL in the generated 330 specification and the type of Office PAL to be included.

Thus, in one example, the predefined table includes ten lines. Each line pertains to one of ten deciles of the users and gives the daily number of hours spent by range and a recommended Office PAL if any, for that decile.

9) Sport PAL design module 93.

One of the fastest growing PAL categories are Sport PAL which are PAL specifically designed for Sport or for specific sports such as: Golf PAL, Soccer PAL, and Running PAL.

Optionally, the Sport PAL design module 93 of the eyewear specification generator 103 of system 1000 chooses Sport PAL for the specification, on basis of the sport with which the user is engaged according to activity type and duration index 60.

Thus, the Sport PAL design module 93 may include Sport PAL (say a specific Golf PAL) when the activity type and duration index reveals that the user spends more than three hours daily, playing Golf.

III. Frame Type Design Module 95

As indicated above according to some embodiments of the present invention the generated 330 specification may additionally or alternatively include a specific spectacles frame material or design, which may be selected for example on basis of the Activity Type and Duration Indices 60 of the user. For instance in case the Activity Type and Duration Indices 60 indicate that the use spends his time in particular activities which may require specific frames (e.g. playing basketball, cycling, skiing, etc.) the frame type design module 95 may select appropriate frame of predetermined type and/or shape and/or material to match these particular activities with which the user is engaged. For example, Basketball players usually need glasses having wide view options.

To this end the system may include reference frame data stored in a reference database/storage and including data indicative of various frame types and activities to which they are suitable, and possibly also the degree of matching between each frame type and activity. The frame type design module 95 may be configured and operable for determining on or more frames for at least one eyewear specification of the user which will be optimally suitable for the one or more activities with which the user should be engaged when using the eyewear of the particular eyewear specification.

IV. Lens Material Design Module 97

As indicated above according to some embodiments of the present invention the generated 330 specification may additionally or alternatively include material data indicating specific material or material type/family (e.g. glass/plastic) to be used in the lenses of the eyewear. The lens material may be selected for example on basis of the Activity Type and Duration Indices 60 of the user (e.g. sport activities may require non-breakable materials such as plastics while for office activities materials of higher refractive indices may be preferred). Alternatively or additionally the lens material may be selected for example on basis of the weather indices 70 in order to prevent lens's fog in case of certain specific values of weather indices indicate. Activity Type and Accordingly the Lens Material design module 97 may select appropriate lens material for any specific eyewear specification prepared for the user such that the used material is suitable for the particular activities with which the user is engaged.

As indicated above according to some embodiments of the present invention the system 1000 further includes a production/manufacturing specification/file Generator 106.

Optionally, the system further includes a—Production Specification/file Generator 106 adapted for processing the eyewear specification obtained module 103 together with input data (e.g. personal user data) indicative of the user's eyesight prescription and possibly also including data indicative of the face structure of the user to determine an eyewear production (manufacturing) specification based on the above.

To this end according to some embodiments the system 1000 includes Eye sight Prescription Data Provider 140 which is configured and operable for providing data (e.g. data received from the user) indicative of the eye prescription of the user. For instance module 140 may be associated with a user input module 142 and/or with a data retriever 144 (e.g. OCR) adapted or obtaining the user prescription.

In some embodiments the system 1000 further includes a Face Structure Data Provider 150 as shown in the figure. This is exemplified in self-explanatory manner in the figure and includes a camera for receiving g facial image of the user, and an image facial analyzer 154 adapted to determine such properties as the interpupillary distance 156, the height of the user's nose bridge 157, and/or the widths of the user's face 157 based on an image of the user.

The generated eyewear manufacturing specification may be communicated to a remote party (say to an optical manufacturer of glasses or lenses), to a remote 3D (three dimensional) Printer, etc.

Optionally, the generated eyewear manufacturing specification are presented to the user in a GUI (Graphical User Interface), say on a screen of the user's smart cellular phone—say by the GUI manager of system 1000, as described in further detail hereinabove.

Optionally, the generated eyewear manufacturing specification is in a form of a file generated in a format readable by a manufacturing machine (or an array of machines)—say an input file for a manufacturing machine such as a 3D Printer or one of the manufacturing machines in current use by the optical industry, as known in the art.

The parts of the specification in the file readable by the manufacturing machine may thus include, but are not limited to, for example:

1. Vision Prescription—an exemplary prescription may consist of:

1.1. Lens diameter—derived from the frame type and shape.

1.2. Sphere—This indicates the amount of lens power, measured in diopters (D) (Unit of measure for the refractive (light-bending) power of a lens), prescribed to correct near-sightedness or farsightedness. If including a minus sign (−), the user is nearsighted; if including a plus sign (+) or not preceded by any of those signs, the user is farsighted.

1.3. Cylinder—This indicates the amount of lens power for astigmatism.

1.4. Axis—This describes the lens meridian that contains no cylinder power to correct astigmatism.

1.5. Add—indicates multi-focal sub-prescription.

1.6. Prism—This is the amount of prismatic power, measured in prism diopters prescribed to compensate for eye alignment problems (say in units and up\down\in\out direction indications).

2. Lens type—multi\bi\single focal.

3. Lens Index—Lens thickness.

4. Color—lens color, transparency percentage, etc.

5. Base Material—Mineral (say glass), Acrylic, Polymeric (say Polycarbonate), etc.

6. Pre-processed Base Material—base material which is already pre-processed for production purposes, say by molding into pre-prepared plates.

7. Filters and coatings—such as: colors (say gradient), UV protection (whether in Coating Type or in Material Type), blue light coating, polarizer (anti-glare coating to material type), Anti-Fog coating, etc.

8. PAL (Progressive Addition Lenses) Design—specific design of lens in order to support multiple focal points for different usage, activity types and needs.

9. Measures—face fitting parameters such as Left & Right PD (Pupil Distance), H (Height from pupil to lens bottom), A (Lens Width), B (Lens Height), D (Bridge distance).

10. Frame type—Plastic, Frameless, etc.

11. Assembly instructions—the production process may include assembling of the complete vision glasses (i.e. lenses manufacturing, assembling of the lenses to the frame, or both).

12. Frame type cut—say instructions to cut the lenses so as to fit a specific frame type, measure, etc.

For example, the generation of the manufacturing specification/file may be additionally based on the user's average temperature indicator, percent indoors indictor, indoors/outdoors indicator, a time spent by the user at specific locations—say at a Golf Club, Gymnasium, etc., or any combination thereof, as described in further detail hereinabove.

Optionally, the generated manufacturing specification further includes data such as, for example, vision prescription data, vision lenses type, measures, frame type, frame shape, materials, filter types, coating types, etc. Optionally, this data is input by the user, input from a file provided by the user or by another party (say an Optometrist or Physician), etc.

Optionally, the file in the machine readable format is communicated to a computer in control of a manufacturing party's manufacturing machine or array of manufacturing machines, over a wireless or wired communication channel, through a communication channel in a production facility, over the internet, etc.

The file may also be input to the manufacturing machine or a computer which controls the manufacturing machine from a smart phone or a computer in use by the user, by an optical store, etc.—say as a file, an email attachment, etc., either automatically or manually (say upon a user's pushing of a specific button in a GUI).

Reference is now made to FIG. 4A-4D, which are simplified diagrams graphically illustrating accelerometer signals related to different activity types, according to an exemplary embodiment of the present invention.

The movement type indicator gives an indication on the type of physical activity as per an analysis of the user's movement per a predefined time frame, say per minute (i.e. for each minute of measurement)—say that the user's is static, driving, walking, running, sailing, etc., as described in further detail hereinabove.

Optionally, the behavioral index deriver calculates the movement type indicator on basis of values measured using one or more accelerometers, say using a pre-trained Neural Network (NN) or Deep Neural Network (DNN) Model, etc.

Thus, in one example, for a time frame of sixty seconds, the behavioral index deriver collects the values measured say at each one of the sixty seconds by an accelerometer installed on the user's mobile device, say together with the indoors/outdoors indicators and the speed indicators for those seconds.

Then, in the example, the behavioral index deriver sends the collected values and indicators to a remote classification engine—say a one based a DNN or an NN Model, as known in the art.

The remote classification engine determines a movement type—say of driving, walking, running, sailing, etc.—based on the indicators and values, and sends the determined movement type back, for the behavioral index deriver to set the movement type indicator with.

For example, the user's smart phone accelerometer may generate three continuous signals, each signal reflecting a movement of the phone (and hence the user) in a respective one of three orthogonal coordinates.

As illustrated by FIG. 4A-4D, when depicted as a triad of waveform graphs, the signal generated by the accelerometer upon different movement types of the user are likely to differ significantly.

Thus the accelerometer is likely to generate one set of signals 4A when the user walks, a different set of signals 4B when the user cycles, a different set of signals 4C when the user climbs stairs, and a yet different set of signals 4D when the user sits at the user's office.

The Neural Network (NN) or Deep Neural Network (DNN) Model may be derived from accelerometer signals received for different users, as known in the art.

Consequently, the remote classification engine may be able to use the derived model for determining the user's movement type—say one of walking, cycling, stairs climbing, or sitting, based on the signals of the accelerometer, for the behavioral index deriver to set the movement type indicator with, as described in further detail hereinabove.

Figure 5A:
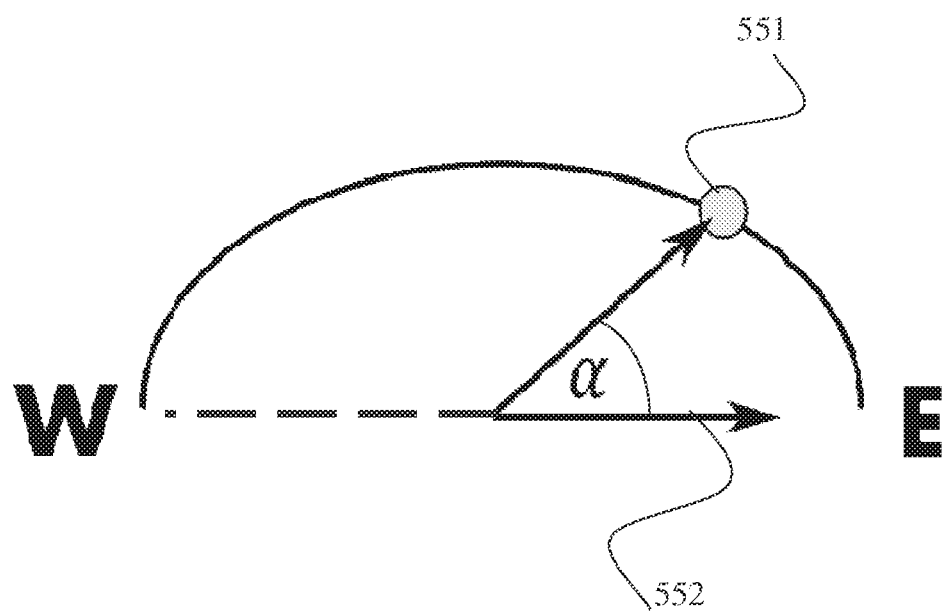
FIG. 5A is a first block diagram schematically illustrating a calculation of a Sun Glare Estimate, according to an exemplary embodiment of the present invention.
Figure 5B:
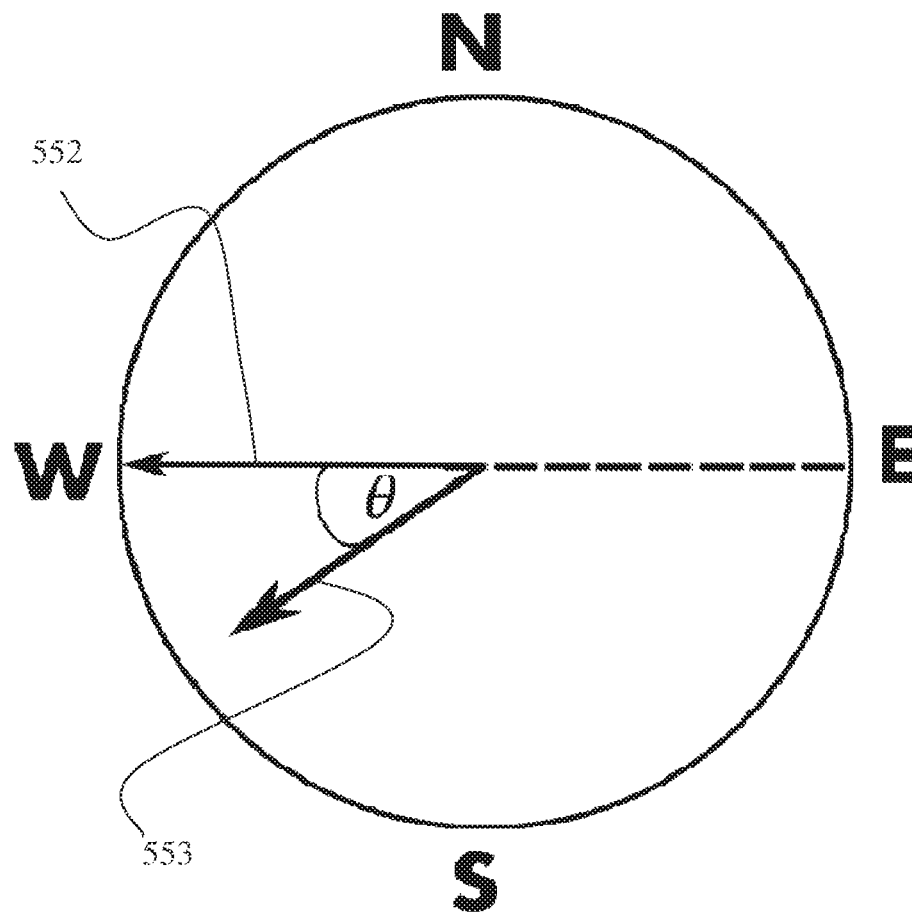
FIG. 5B is a second block diagram schematically illustrating a calculation of a Sun-Glare Estimate, according to an exemplary embodiment of the present invention.

Reference is now made to FIG. 5A and FIG. 5B, which are block diagrams schematically illustrating a calculation of Sun Glare Estimate, according to an exemplary embodiment of the present invention.

According to one exemplary embodiment, a sun glare estimate is calculated, say by the behavioral index deriver 102 of system 1000, according to an exemplary sun glare calculation method in which there is calculated a continuous sun glare path parameter.

As illustrated using FIG. 5A, the continuous sun glare path parameter's value represents the sun's 551 glare as a function of the position of the sun 551 along a path assumed to stretch from east (at sunrise) to west (at sunset), along a circular arch, over the user's general geographical area (say a city in which the user resides).

According to the method, during daylight hours, the sun glare path parameter's value is given by: $S=0.5\times(1+abs(\sin\alpha))$, where S denotes the sun glare path parameter and a denotes the angle between the position of the sun 551 and a straight line 552 aligned in a West to East direction, on a thus assumed (for this calculation) to be planar geographical area of the user.

In the example, the value of a varies from (+90°) to (−90°) and is derived from publically available data on times of Sunrise and Sunset in the user's geographical area (say city), say from one of the internet weather websites.

The value of $\alpha$ may be derived, for example, by: $\alpha=90°-180°\times(t-\text{Sunrise Time})/(\text{Sunset Time}-\text{Sunrise Time})$, where t denotes the current time of the day (say 10:25 or 13:50).

Thus, for example, at noon when the sun is at its highest elevation, $\alpha=0°$ and $S=0.5$. However, shortly before Sunset or shortly after Sunrise—i.e. when the impact of sun glare on a user who faces the sun is maximal, $\alpha=\sim(+90°)$ or $\sim(-90°)$ and $S=\sim1$.

In order to calculate the sun glare estimate, the exemplary method further takes into consideration the user's direction of movement.

Indeed, if the user moves (say drives) from west to east in a morning hour, just after the sun rises, the user faces the sun substantially directly and is thus likely to experiences very significant sun glare. However, if in that time, the user rather drives from east to west—i.e. with his back to the sun, the user's is not likely to experience significant sun glare.

As illustrated using FIG. 5B, the exemplary method represents the user's direction of movement using the angle denoted θ—which is the angle between the straight line 552 aligned in a West to East direction and the user's direction of movement 553.

The angle's θ value may vary for example, from 0° when the user's direction 553 of movement is straight to the North, to 90° when the direction 553 is straight to the East, to 180° when the direction 553 is straightly to the South, and to (+270°) or (−90°) when the direction 553 is straightly to the West.

The exemplary method further calculates a user direction parameter.

When the user is present in the Earth's Northern Hemisphere and the value of θ is between (−90°) and (90°), the user direction parameter is given by: $U=0.25\times(1+3\times abs(Sin(\theta)))$, where U denotes the user direction parameter.

When the user is present in the Earth's Northern Hemisphere and the value of θ is between (90°) and (270°), the user direction parameter is given by: $U=0.5\times(1+abs(Sin(\theta)))$, where U denotes the user direction parameter.

However, when the user is rather present in the Earth's Southern Hemisphere and the value of θ is between (−90) and (90°), the user direction parameter is given by: $U=0.5\times(1+abs(Sin(\theta)))$, where U denotes the user direction parameter.

When the user is present in the Earth's Southern Hemisphere and the value of θ is between (90°) and (270°), the user direction parameter is given by: $U=0.25\times(1+3\times abs(Sin(\theta)))$, where U denotes the user direction parameter.

Then, when the signs of the Sin (θ) and Sin (α) are the same (i.e. when both signs are positive or both signs are negative), the exemplary method calculates the sun glare estimate by multiplying the user direction parameter by the sun glare path parameter: $E=S\times U$, where E denotes the sun glare estimate.

However, when the signs of the Sin (θ) and Sin (α) are different, in the exemplary method, the sun glare estimate is given by: $E=(1-S)\times U$, where E denotes the sun glare estimate Turning back to FIGS. 1A, 1B, 2B, 3A and 3B described above is noted that system 1000 which is illustrated and described with relation to these figures and the modules thereof may be implemented system by hardware (e.g. computer hardware including one or more processor(s), memories storage devices and/or communication modules and/or analog circuitry) or by software embedded in a non-transitory computer readable medium storing computer processor executable instructions for performing steps of automatic eyewear measurement and specification, according to the exemplary embodiments of the present invention described above, or by a combination of such hardware and software components.

According to an exemplary embodiment of the present invention, there is provided a non-transitory computer readable medium, such as a Micro SD (Secure Digital) Card, a CD-ROM, a USB-Memory, a Hard Disk Drive (HDD), a Solid State Drive (SSD), etc. The computer readable medium may store computer executable instructions, for performing steps of automatic eyewear measurement and specification, as described above for example with reference to the exemplary method 300 illustrated using FIG. 3. The instructions may be executed on one or more computer processors—say on a computer processor of a user carried mobile device, on a computer processor of a server computer, etc., or any combination thereof. For carrying out the steps, at least one of the computer processors communicates with one or more mobile sensors over a wireless or over a wired connection, as described in further detail hereinabove. The mobile sensors may include for example, one or more sensors installed on a device carried on a mobile device of the user, one or more sensors worn by the user and connected to the device (say a mobile device or desktop computer) over a wired or a wireless connection, etc., or any combination thereof.

It is expected that during the life of this patent many relevant devices and systems will be developed and the scope of the terms herein, particularly of the terms "Computer", "Sensor", "Smart Phone", "Smart Watch", "Server Computer", "GPS receiver", "Accelerometer", "Photometer", "Camera", "Compass", "Clock", "Wi-Fi" "Communications Card", "Cellular Telephony", "3G", "4G", "LTE", "3D Printer", "Database", "Web Site", "Application", "E-SPF", "Anti-Glare Coating", "Anti-Reflection Coating", "Photochromic Lenses", "HEY Protection Coating", "Anti-Fog Coating", "PAL", "Lenses", and "Eyewear", is intended to include all such new technologies a priori.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A system for automatic eyewear measurement and specification, comprising:
a value measurer, in communication with at least one mobile sensor carried by a user, configured to obtain a plurality of measured values using said at least one mobile sensor; and
a behavioral index deriver, in communication with said value measurer, configured to derive at least one behavioral index indicative of an eye usage, using the measured values;
wherein the behavioral index deriver is configured and operable for monitoring a behavior of said user during a certain behavioral monitoring time period, and to thereby derive said at least one behavioral index, as an index indicative of the eye usage of the user during the certain behavioral monitoring time period; and wherein during said behavioral monitoring time period:
(a) the value measurer is configured and operable to obtained sensory data indicative of the values measured by said at least one mobile sensor during a plurality of spaced apart interleaved time intervals within said behavioral monitoring time period; and (b) said behavioral index deriver is configured and operable to carry out the following in order to derive said at least one behavioral index:
   obtain sensory data indicative of the measured values obtained from said at least one sensor during the spaced apart time intervals;
   utilize the sensory data of each respective time interval to determine low level indicators pertaining to behavioral characteristics of the user during the respective time interval; and
   utilize the low level indicators pertaining to the plurality of time intervals of said behavioral monitoring time period, to determine thereby at least one behavioral index indicative of a behavioral characteristic of the user.

2. The system of claim 1, comprising an eyewear specification generator, in communication with said behavioral index deriver, configured to generate an eyewear specification for the user, using the at least one derived behavioral index based on the monitored behavior of said user and without requiring data input from the user.

3. The system of claim 2, wherein said eyewear specification generator is configured and operable for generating said eyewear specification such that said eyewear specification includes data indicative of at least one recommended eyewear for the user including one or more of the following:
   data indicative of at least one optical lens design suitable for the user based on behavioral characteristics of the user;
   data indicative of one or more lens coatings selected based on behavioral characteristics of the user; and
   data indicative of at least one of the following: eyewear frame type and lens material; and wherein said at least one of the eyewear frame type and the lens material is selected based on behavioral characteristics of the user.

4. The system of claim 2, comprising an eyewear manufacturing specification generator, configured and operable for utilizing said eyewear specification and receiving personal user data indicative of at least one of an eyesight prescription of said user and face structure of said user, and generating an eyewear manufacturing specification for manufacturing at least one piece of eyewear for said user based on the eyewear specification and said personal data.

5. A system for automatic eyewear measurement and specification, comprising:
   a value measurer, in communication with at least one mobile sensor carried by a user, configured to obtain a plurality of measured values using said at least one mobile sensor; and
   a behavioral index deriver, in communication with said value measurer, configured to derive at least one behavioral index indicative of air eye usage, using the measured values;
   wherein the at least one mobile sensor carried by a user includes at least an accelerometer providing sensory data indicative of the user's activity; and wherein said value measured is adapted for utilizing said at least one mobile sensor to determine data indicative of at least one low level indicator indicative of movement of the user.

6. A system for automatic eyewear measurement and specification, comprising:
   a value measurer, in communication with at least one mobile sensor carried by a user, configured to obtain a plurality of measured values using said at least one mobile sensor; and
   a behavioral index deriver, in communication with said value measurer, configured to derive at least one behavioral index indicative of an eye usage, using the measured values;
   wherein the at least one mobile sensor carried by a user includes at least a positioning module adapted to provide data indicative of a location of the user; and wherein the system includes a data provider module configured and operable for connecting to data services over a data network to determine at least one of lighting and weather conditions at a geographical location of the user determined by said positioning sensor.

7. The system of claim 6, configured and operable to determine data indicative of an indoors or outdoors environment of the user during a certain time interval and utilizing said data in conjunction with data indicative of the at least one of lighting and weather conditions at the geographical location of the user, to estimate at least one of lighting and weather conditions to which the user is exposed during the respective tune interval.

8. A system for automatic eyewear measurement and specification, comprising:
   a value measurer, in communication with at least one mobile sensor carried by a user, configured to obtain a plurality of measured values using said at least one mobile sensor; and
   a behavioral index deriver, in communication with said value measurer, configured to derive at least one behavioral index indicative of an eye usage, using the measured values;
   wherein the system is configured and operable for implementation in a mobile device of the user which includes the at least one mobile sensor, and wherein said value measurer operates at spaced apart time intervals for measuring the plurality of values; and
   wherein the system is adapted to deactivate said at least one mobile sensor at sleep periods between said spaced apart time intervals in order to reduce energy consumption of said mobile sensor.

9. A method for automatic eyewear measurement, the method comprising the steps of:
   a) measuring values obtained from at least one mobile sensor carried by a user; and
   b) processing the measured values and deriving at least one behavioral index indicative of an eye usage using the received data;
   wherein the method comprises monitoring a behavior of said user during a certain behavioral monitoring time period, deriving said at least one behavioral index, as an index indicative of the eye usage of the user during the certain behavioral monitoring time period; and
   wherein said processing comprises:
      obtaining sensory data indicative of the values measured by said at least one sensor in a plurality of spaced apart interleaved time intervals during said behavioral monitoring time period;
      utilizing the sensory data of each time interval to determine low level indicators pertaining to behavioral characteristics of the user during the respective time interval; and
      utilizing the low level indicators pertaining to the plurality of spaced apart interleaved time intervals to determine at least one behavioral index indicative of a behavioral characteristic of the user during the behavioral monitoring period extending over the plurality of the spaced apart time intervals.

10. The method of claim 9, further comprising generating of an eyewear specification for the user based on said at least one behavioral index derived from the measured values obtained from the at least one mobile sensor and wherein said generating of the eyewear specification is performed by monitoring a behavior of said user and without requiring data input from the user.

11. The method of claim 9, comprising generating an eyewear specification for the user including data indicative at least one optical lens design suitable for the user whereby said at least one optical lens design is determined based on said at least one behavioral index.

12. A non-transitory computer readable medium storing computer processor executable instructions for performing the method according to claim 9.

13. A method for automatic eyewear measurement, the method comprising the steps of:
 a) measuring values obtained from at least one mobile sensor carried by a user; and
 b) processing the measured values and deriving at least one behavioral index indicative of an eye usage using the received data;
 wherein the method comprises obtaining said measured values from at least a positioning module adapted to provide data indicative of a geographic location of the user; and
 wherein the method comprises utilizing said geographic location and connecting to data services over a data network to determine low level indicators indicative of at least one of lighting and weather conditions at the geographic location of the user.

14. The method of claim 13, further comprising determining data indicative of an indoors or outdoors environment of the user, and utilizing said data of the indoors or outdoors environment of the user in conjunction with data indicative of the at least one of lighting and weather conditions at the geographical location of the user, to estimate at least one of lighting and weather conditions to which the user is exposed during a respective time interval.

15. A non-transitory computer readable medium storing computer processor executable instructions for performing the method according to claim 13.

16. A method for automatic eyewear measurement, the method comprising the steps of:
 a) measuring values obtained from at least one mobile sensor carried by a user; and
 b) processing the measured values and deriving at least one behavioral index indicative of an eye usage using the received data;
 wherein the method is adapted for execution in a mobile device of the user which includes the at least one mobile sensor; and wherein said measuring is carried out at spaced apart time intervals and further comprises deactivating said at least one mobile sensor at sleep periods between said spaced apart time intervals in order to reduce energy consumption of said mobile sensor.

17. A non-transitory computer readable medium storing computer processor executable instructions for performing the method according to claim 16.

18. A method for automatic eyewear measurement, the method comprising the steps of:
 a) measuring values obtained from at least one mobile sensor carried by a user; and
 b) processing the measured values and deriving at least one behavioral index indicative of an eye usage using the received data;
 wherein the method comprises generating an eyewear specification for the user including data indicative of one or more lens coatings to be included in the eyewear of the user whereby said one or more lens coatings are selected based on said behavioral index.

19. A method for automatic eyewear measurement, the method comprising the steps of:
 a) measuring values obtained from at least one mobile sensor carried by a user; and
 b) processing the measured values and deriving at least one behavioral index indicative of an eye usage using the received data;
 wherein the method comprises generating an eyewear specification for the user including data indicative of at least one of the following:
eyewear frame type and lens material; and wherein said at least one of the eyewear frame type and the lens material is selected based on said behavioral index of the user.

* * * * *